United States Patent
Heaney et al.

(10) Patent No.: US 6,673,823 B2
(45) Date of Patent: Jan. 6, 2004

(54) USE OF PEROXISOME PROLIFERATOR ACTIVATED RECEPTOR (PPAR)-γ LIGANDS AS A TREATMENT FOR PITUITARY TUMORS AND ASSOCIATED CONDITIONS, SUCH AS CUSHING'S SYNDROME

(75) Inventors: Anthony P. Heaney, Los Angeles, CA (US); Shlomo Melmed, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 59 days.

(21) Appl. No.: 10/163,053

(22) Filed: Jun. 4, 2002

(65) Prior Publication Data

US 2003/0225139 A1 Dec. 4, 2003

(51) Int. Cl.$^7$ ................................. A61K 31/44
(52) U.S. Cl. ........................ 514/369; 569/342
(58) Field of Search .................. 514/369, 342

(56) References Cited

U.S. PATENT DOCUMENTS

| | | | | |
|---|---|---|---|---|
| 4,710,370 A | * | 12/1987 | Macy | ................ 435/14 |
| 5,814,647 A | | 9/1998 | Urban et al. | |
| 6,207,690 B1 | | 3/2001 | Urban et al. | |

OTHER PUBLICATIONS

Sylvester et al, Int. J. Cancer, vol. 42(2), pp. 289–294 (abstract) Aug. 1988.*
Ip et al, Cancer Res., vol. 46(4 Pt 1) pp. 1735–1740, (abstract) Apr. 1986.*
Bevan, J. S., et al., Non–Functioning Pituitary Adenomas do not Regress During Bromocriptine Therapy but Possess Membrane–Bound Dopamine Receptors Which Bind Bromocriptine, *Clinical Endocrinology*, vol. 25, pp. 561–572, (1986).
Brada, M., et al., The long–term efficacy of conservative surgery and radiotherapy in the control of pituitary adenomas, *Clinical Endocrinology*, vol. 38, pp. 571–578 (1993).
Chandrasekharappa, S. C., et al., Positional cloning of the gene for multiple endocrine neoplasia– type 1, *Science*, vol. 276, pp. 404–407 (1997). Abstract Only.
Colao, A., et al., New medial approaches in pituitary adenomas, *Horm. Res.*, 53Suppl3:76–87 (2000). Abstract Only.
Elstner, E., et al., Ligands for peroxisome proliferator–activated receptor–γ and retinoic acid receptor inhibit growth and induce apoptosis of human breast cancer cells in vitro and in BNX mice, *Proc. National Acad. Sci. USA*, vol. 95, pp. 8806–8811 (1998).
Findling, J. W., et al., Diagnosis and differential diagnosis of Cushing's syndrome, *Endocrinology Metabolism Clin. of North America*, vol. 30, pp. 729–747 (2001). Abstract Only.

Forman, B. M., et al., 15–Deoxy–delta 12, 14–prostaglandin J2 is a ligand for the adipocyte determination factor PPAR gamma, *Cell*, 83 (5):803–12 (1995). Abstract Only.
Giustina, A., et al., Criteria for cure of acromegaly: a consensus statement, *Journal of Clinical Endocrinology Metabolism*, 85 (2):526–529 (2000). Abstract Only.
Göke, R., et al., Regulation of TRAIL–Induced Apoptosis by Transcription Factors, *Cell. Immunol.* 201:77–81 (2000).
Hoybye, C., et al., Adrenocorticotrophic hormone–producing pituitary tumors: 12 to 22–year follow–up after treatment with sterotactic radiosurgery, *Neurosurgery*, 49(2):284–291 (2001). Abstract Only.
Issemann, I., et al., Activation of a member of the steroid hormone receptor superfamily by peroxisome proliferators, *Nature*, vol. 347. pp. 645–650 (1990).
Jiang, C., et al., PPAR–gamma agonists inhibit production of monocyte inflammatory cytokines, *Nature*, 391(6662):82–86 (1998). Abstract Only.
Kliewer, S. A., et al., Convergence of 9–cis retinoic acid and peroxisome proliferator signalling pathways through heterodimer formation of their receptors, *Nature*, vol. 358, pp. 771–774 (1992).
Kliewer, S. A., et al., A prostaglandin J2 metabolite binds peroxisome proliferator–activated receptor gamma and promotes adipocyte differentiation, *Cell*, 83(5):813–819 (1995). Abstract Only.
Kreutzer, J., et al., Surgical Management of GH–Secreting Pituitary Adenomas: An Outcome Study Using Modern Remission Criteria, *Journal of Clinical Endocrinology & Metabolism*, vol. 86, pp. 4072–4077 (2001).
Krieger, D. T., et al., Cyproheptadine–Induced Remission of Cushing's Disease, *New England Journal of Medicine*, vol. 293, pp. 893–896 (1975).
Kubota, T., et al., Ligand for Peroxisome Proliferator–activated Receptor γ (Troglitazone) Has Potent Antitumor Effect Against Human Prostate Cancer Both in Vitro and in Vivo, *Cancer Research*, vol. 58, pp. 3344–3352 (1998).
Larsson, C., et al., Multiple endocrine neoplasia type 1 gene maps to chromosome 11 and is lost in insulinoma, *Nature*, 322(6159):85–87 (1988). Abstract Only.

(List continued on next page.)

Primary Examiner—James H Reamer

(57) ABSTRACT

Disclosed is a method for treating a pituitary tumor in a mammal, employing the administration of a peroxisome proliferator activated receptor gamma ligand (also known as "peroxisome proliferating-activator receptor gamma" or "PPAR-γ"). In some embodiments, the peroxisome proliferator activated receptor gamma ligand is a thiazolidinedione compound. Also disclosed are methods for preventing the formation of a pituitary tumor in a mammal and for preventing the recurrence of a pituitary tumor in a mammal. Further disclosed is a method for treating a mammal exhibiting one or more symptoms of Cushing's syndrome.

15 Claims, 17 Drawing Sheets

OTHER PUBLICATIONS

Lyons, J., et al., Two G protein oncogenes in human endocrine tumors, *Science,* 249(4969):655–659 (1990). Abstract Only.

Mampalam, T. J., et al., Transsphenoidal microsurgery for Cushing's disease. A report of 216 cases, *Ann. Internal Medicine,* 109(6):487–493 (1988). Abstract Only.

Motomura, W., et al., Activation of Peroxisome Proliferator-activated Receptor γ by Troglitazone Inhibits Cell Growth through the Increase of $p27^{KiP1}$ in Human Pancreatic Carcinoma Cells, *Cancer Res.* 60:5558–64 (2000).

Nobels, F. R., et al., Long–term treatment with the dopamine agonist quinagolide of patients with clincally non–functioning pituitary adenoma, *European Journal of Endocrinology,* vol. 143, pp. 615–621 (2000).

Oldfield, E. W., et al., Petrosal sinus sampling with and without corticotrophin–releasing hormone for the differential diagnosis of Cushing's syndrome, *New England Journal of Medicine,* 325(13):897–905 (1991). Abstract Only.

Orth, D. N., Cushing's syndrome, *New England Journal of Medicine,* 332(12):791–803 (1995). Abstract Only.

Palmer, C. N., et al., Interaction of the peroxisome proliferator–activated receptor alpha with the retinoid X receptor alpha unmasks a cryptic peroxisome proliferator response element that overlaps an ARP–1–binding site in the CYP4A6 promoter, *Journal of Biological Chemistry,* 269(27):18083–9 (1994). Abstract Only.

Ricote, M., et al., The peroxisome proliferator–activated receptor–γ is a negative regulator of macrophage activation, *Nature,* vol. 391, pp. 79–82 (1998).

Ross, E. J., et al., Cushing's Syndrome– Killing Disease: Discrimatory Value of Signs and Symptoms Aiding Early DiagnosiS, *Lancet,* vol. 2, pp. 646–649 (1982).

Saltiel, A. R., et al., Thiazolidinediones in the Treatment of Insulin Resistance and Type II Diabetes, *Diabetes,* vol. 45, pp. 1661–1669 (1996).

Sarraf, P., et al., Differentiation and reversal of malignant changes in colon cancer through PPARγ, *Nat. Med.,* vol. 4, pp. 1046–1052 (1998).

Schoonjans, K., et al., Peroxisome proliferator–activated receptors, orphans with ligands and functions, *Current Opinion Lipidol,* vol. 8, pp. 159–166 (1997).

Shimon, I., et al., Management of Pituitary Tumors, *Ann. Internal Medicine,* vol. 129, pp. 472–483 (1998).

Simmons, N. E., et al., Serum cortisol response to transphenoidal surgery for Cushing disease, *Journal of Neurosurgery,* 95(1):1–8 (2001). Abstract Only.

Sonino, N., The use of Ketoconazole as an Inhibitor of Steroid Production, *New England Journal of Medicine,* vol. 317, pp. 812–818 (1987).

Spiegelman, B. M., PPAR–γ. Adipogenic Regulator and Thiazolidinedione Receptor, *Diabetes,* vol. 47, pp. 507–514 (1998).

Staels, B., et al., Activation of human aortic smooth–muscle cells is inhibited by PPAR–α but not PPAR–γ activators, *Nature,* vol. 393, pp. 790–793 (1998).

Stratakis, C. A., et al., Carney complex, familial multiple neoplasia and lentiginosis syndrome. Analysis of 11 kindreds and linkage to the short arm of chromosome 2, *Journal of Clinical Investigation,* 97(3):699–705 (1996).

Sugimura, A., et al., Troglitazone Suppresses Cell Growth of Myeloid Leukemia Cell Lines by Induction of p21WAF1/CIP1 Cyclin–Dependent Kinase Inhibitor, *Biochem. Biophys. Res. Comm.* vol. 26, pp. 833–837 (1999).

Tontonoz, P., et al., mPPARγ2: tissue–specific regulator of and adipocyte enhancer, *Genes Dev.,* vol. 8, pp. 1224–1234 (1994).

Trainer, P. J., et al., Cushing's syndrome. Therapy directed at the adrenal glands, *Endocrinology Metab. Clinic of North Am.,* 23(3):571–584 (1994). Abstract Only.

Trainer, P. J., et al., Transsphenoidal resection in Cushing's disease: undetectable serum cortisol as the definition of successful treatment, *Clinical Endocrinology,* vol. 38, pp. 73–78 (1993).

Vale, W., et al., Characterization of a 41–Residue Ovine Hypothalamic Peptide That Stimulates Secretion of Corticotropin and β–Endorphin, *Science,* vol. 213, pp. 1394–1397 (1981).

Wakino, S., et al., Peroxisome Proliferator–activated receptor γ Ligands Inhibit Retinoblastoma Phosphorlyation and $G_1 \rightarrow S$ Transition in Vascular Smooth Muscle Cells, *J. Biol. Chem.* vol. 275, pp. 22435–22441 (2000).

Web Page Abstract, "Pituitary Tumor & Neuroendocrine Diseases & Disorders", http://www.neurosurgery.medsch.ucla.edu/redirect/Pituitary/Pituitary/PituitaryDis_6.html. Nov. 7, 2002.

Xin, X., et al., Peroxisome Proliferator–Activated Receptor γ Ligands are Potent Inhibitors of Angiogenesis in Vitro and in Vivo, *Journal of Biological Chemistry,* vol. 274, pp. 9116–9121 (1999).

\* cited by examiner

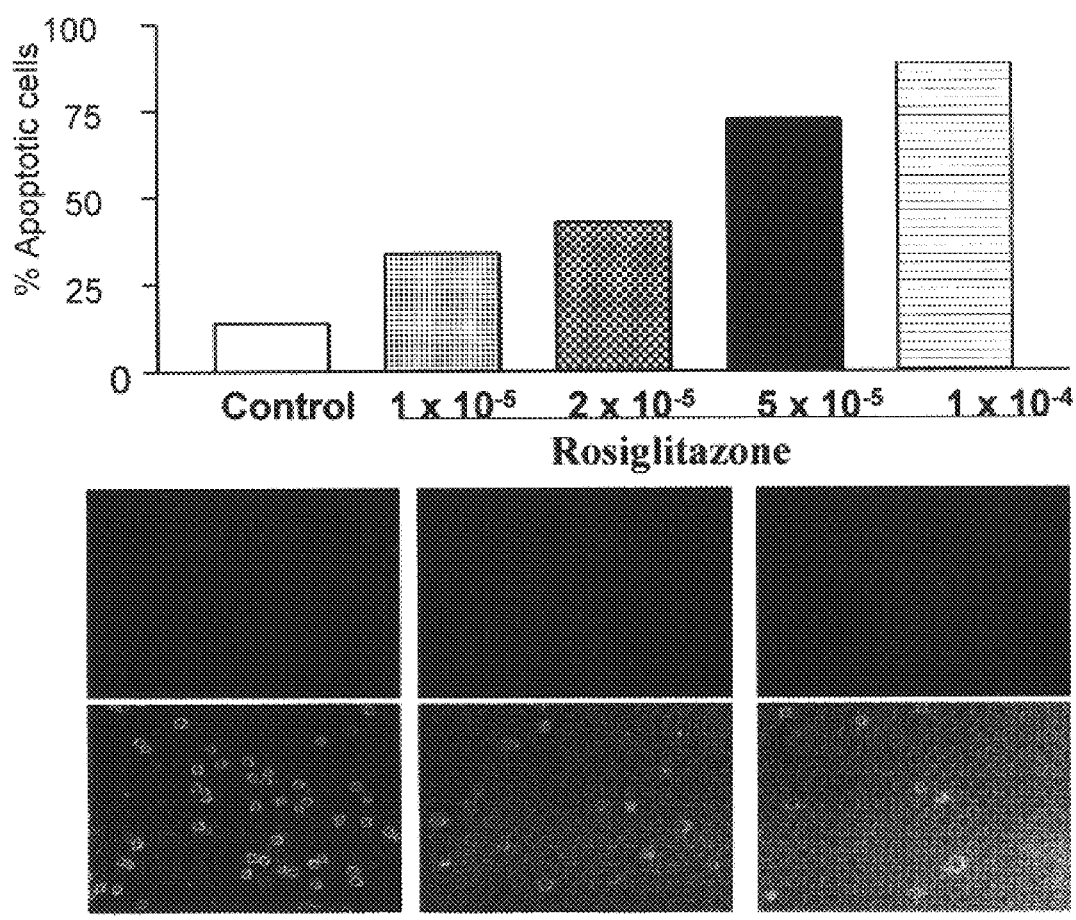

* p = 0.0002

** p = 0.004

USE OF PEROXISOME PROLIFERATOR ACTIVATED RECEPTOR (PPAR)-γ LIGANDS AS A TREATMENT FOR PITUITARY TUMORS AND ASSOCIATED CONDITIONS, SUCH AS CUSHING'S SYNDROME

The U.S. Government has a paid-up license in this invention and the right in limited circumstances to require the patent owner to license others on reasonable terms as provided for by the terms of Contract CA75979, awarded by the National Institutes of Health.

BACKGROUND OF THE INVENTION

Throughout the application, various publications are referenced in parentheses. The disclosures of these publications in their entireties are hereby incorporated by reference in the application in order to more fully describe the state of the art to which this invention pertains.

1. Field of the Invention

The present invention is related to the medical arts, in particular to the treatment of pituitary tumors.

2. Discussion of the Related Art

The pituitary gland is divided into two primary regions, a larger anterior region (adenohypophysis), which constitutes 80 percent of the pituitary by weight, and a smaller posterior region (neurohypophysis). This gland connects to a region of the brain called the hypothalamus near the pituitary stalk. Because of its close proximity to major intracranial nerves and blood vessels, as well as the vital hormonal control the pituitary gland provides, disorders of the pituitary can cause a wide spectrum of symptoms, both hormonal and neurological. In most instances, pituitary disorders result in the secretion of either too much or too little of one or more hormones typically secreted by the pituitary gland.

The importance of the pituitary gland is amply illustrated by the numerous hormones it produces, i.e., hormones such as Thyroid Stimulating Hormone (TSH), Growth Hormone (GH), Adrenocorticotrophic Hormone (ACTH), Antidiuretic Hormone (ADH), Luteinizing Hormone (LH), Prolactin (PRL), Follicle Stimulating Hormone (FSH), Melanocyte-Stimulating Hormone (MSH), and Oxytocin.

The cells of the anterior lobe synthesize and release several protein hormones necessary for normal growth and development and also stimulate the activity of several target glands. Deviations above or below normal hormone levels of the hormones produced by the anterior lobe can result in any one of a number of disease conditions. For example, excess amounts of the hormone ACTH can result in Cushing's syndrome; an excess production of TSH causes hyperthyroidism; and hypersecretion of GH can result in either acromegaly or gigantism. Conversely, reduced amounts of GH can cause growth hormone deficiency syndrome in adults and children, (characterized by short stature in children). Other hormones controlled by the anterior lobe include LH and FSH, which when affected by a tumor can give rise to sexual symptoms in men and women. Increased production of prolactin can cause abnormal milk production, irregular menses and infertility in women; for men, increased prolactin levels can cause impotence, infertility, feminization and lactation. Tumors affecting the posterior lobe disrupt production of ADH, which may lead to diabetes insipidus; the hormone oxytocin is also secreted from the posterior lobe.

Some pituitary disorders have exhibited a familial predisposition, including, e.g., multiple endocrine neoplasia, Carney complex, and McCune Albright syndrome. (See Larsson, C., et al., M. Multiple endocrine neoplasia type 1 gene maps to chromosome 11 and is lost in insulinoma, Nature 322:85–87 [1988]; Chandrasekharappak, S. C., et al., Positional cloning of the gene for multiple endocrine neoplasia- type 1, Science 276:404–406 [1997]; Stratakis, C. A., et al., Carney complex, familial multiple neoplasia and lentiginosis syndrome. Analysis of kindreds and linkage to the short arm of chromosome 2, J. of Clin. Invest. 97:699–705 [1996]; Lyons J., et al., Two G protein oncogenes in human endocrine tumors, Science 249:655–659 [1990]).

One genre of pituitary disorders is pituitary tumors. A pituitary tumor (adenoma) is a non-cancerous growth that typically affects different hormone-producing regions, depending on its specific location. Pituitary tumors account for about 15% of intracranial tumors, and are associated with significant morbidity due to local compressive effects, hormonal hypersecretion, or treatment-associated endocrine deficiency (Heaney A. P., et al.: Molecular Pathogenesis of Pituitary Tumors. In: Oxford Textbook of Endocrinology, Wass J. A. H. and Shalet S. M., (Eds.), Oxford University Press, Oxford, 2002 (in press)). The great majority of pituitary adenomas are benign, not malignant, and are relatively slow growing. (See UCLA Neurosurgery web site at <www.neurosun.medsch.ucla.edu>). Pituitary tumors may lead to overproduction of one or more of the pituitary hormones. In other instances, pituitary tumors are non-functioning or "endocrine-inactive," meaning that they do not produce excessive hormones.

Non-functioning adenomas are the most commonly encountered pituitary tumors. These tumors fail to secrete hormones, are generally macroadenomas ($\geq 1$ centimeter), and cause high morbidity and ultimately mortality due to visual field loss, headache, and pituitary dysfunction (Shimon, I., et al., Management of Pituitary Tumors, Ann. Intern. Med. 129:472–483 [1998]). Some non-functioning pituitary tumors express dopamine and/ or somatostatin receptors, but response to treatment with dopamine agonists and/ or somatostatin is poor, and their use has largely been discontinued (Nobels, F. R., et al., Long-term treatment with the dopamine agonist quinagolide of patients with clinically non-functioning pituitary adenoma. Eur. J. Endocrinol. 143:615–21 [2000]) and effective drug therapies for non-functioning pituitary tumors do not currently exist. As pituitary tumors enlarge, compression of normal pituitary tissue can occur, resulting in decreased or absent hormone production. This condition is called hypopituitarism and may also result from brain trauma, surgery, bleeding into the pituitary or from radiation therapy to the pituitary.

Examples of pituitary tumors that lead to pituitary hormone hypersecretion are PRL- and GH-secreting pituitary tumors. Dopamine agonists and somatostatin analogs effectively suppress PRL and GH hypersecretion, respectively, and control tumor growth or induce tumor shrinkage in most, but not all, PRL-and GH-secreting pituitary tumors (Shimon, I., et al., Management of Pituitary Tumors, Ann. Intern. Med. 129:472–83 [1998]; Giustina, A., et al., Criteria for cure of acromegaly: a consensus statement, J. Clin. Endocrinol. Metab. 85:526–9 [2000]). A subset of patients with PRL- and GH-secreting pituitary tumors do not respond to such drug treatments or are intolerant of side-effects from these drugs. For unresponsive GH- and PRL-secreting, and non-functioning pituitary tumors, surgery with or without adjuvant radiation is the treatment mainstay, and portends a 50–60% overall control rate in specialized centers (Bevan, J. S., et al., Non-functioning pituitary adenomas do not regress during bromocriptine therapy but possess membrane-bound dopamine receptors which bind bromocriptine, Clin. Endocrinol. 25:561–72 [1986]; Colao, A., et al., New medical approaches in pituitary adenomas, Horm. Res. 53:76–87 [2001]). Although 70% of pituitary microadenomas are successfully resected by transsphenoidal approaches, 25% of PRL-secreting, and 90% of GH-secreting and non-functioning tumors are >1 cm in diameter, and surgical "cure" rates for these macroadenomas are achieved in about a third of patients in specialized centers (Colao, A., et al., New medical approaches in pituitary adenomas, Horm. Res. 53:76–87 [2001]). Tumor recurrence requires pituitary-directed radiation to suppress tumor growth and hormonal levels, but radiation effects may not be manifest for several years, and are ultimately associated with pituitary damage and dysfunction in most patients (Kreutzer J., et al., Surgical management of GH-secreting pituitary adenomas: an outcome study using modern remission criteria, J. Clin. Endocrinol. Metab. 86:4072–7 [2001]).

Another such pituitary tumor that leads to pituitary hormone hypersecretion is an ACTH-secreting pituitary tumor. About 90% of ACTH-secreting pituitary tumors are microadenomas (<1 cm diameter), and cavernous sinus invasion or optic chiasm compression are uncommonly encountered (Ross, E. J., et al., Cushing's syndrome-killing disease: Discrimatory value of signs and symptoms aiding early diagnosis, Lancet 2:646–9 [1982]; Oldfield, E. W., et al., Petrosal sinus sampling with and without corticotrophin-releasing hormone for the differential-diagnosis of Cushing's syndrome, N. Engl. J. Med. 325:897–905 [1991]). Although ACTH-secreting pituitary tumors are rarely invasive, they cause considerable morbibity due to excess glucocorticoid production. ACTH-secreting lesions cause elevated, non-suppressible, ACTH levels, hypercortisolemia, Cushing's syndrome, and varied clinical manifestations, including diabetes, hypertension, muscle weakness, and osteoporosis (Ross . E. J., et al., Cushing's syndrome-killing disease: Discrimatory value of signs and symptoms aiding early diagnosis. Lancet; 2: 646–9 [1982]). Unless treated, the ACTH-secreting pituitary tumors are associated with high morbidity and ultimately mortality (Oldfield E. W., et al., Petrosal sinus sampling with and without corticotrophin-releasing hormone for the differential diagnosis of Cushing's syndrome. N. Engl. J. Med., 1991; 325: 897–905).

Effective drug therapies for ACTH-secreting pituitary tumors do not currently exist. Surgery with or without adjuvant radiation is the treatment mainstay, and portend a 50–60% overall control rate in specialized centers (Simmons, N. E., et al., Serum cortisol response to transphenoidal surgery for Cushing disease, J. Neurosurg. 95:1–8 [2001]; Mampalam, T. J., et al., Transsphenoidal microsurgery for Cushing's disease: A report of 216 cases, Ann. Intern. Med. 109:487–93 [1988]; Hoybye, C., et al., Adrenocorticotrophic hormone-producing pituitary tumors: 12 to 22-year follow-up after treatment with sterotactic radiosurgery, Neurosurgery 49:284–91 [2001]).

Cushing's syndrome is a disease condition in mammals, wherein an increased blood concentration of cortisol (hypercortisolism) or glucocorticoid hormone is present over a long period of time. The most common cause of Cushing's syndrome is excessive production of ACTH by the pituitary gland. ACTH stimulates the growth of the adrenal glands and the secretion of other corticosteroids. This elevated level of ACTH in the bloodstream typically is produced by a pituitary adenoma (Cushing's disease), but in rare instances has a different etiology. Cushing's syndrome resulting from the production of ACTH in a location other than the pituitary gland is known as ectopic Cushing's syndrome. Examples of ectopic sites include thymoma, medullary carcinoma of the thyroid, pheochromocytoma, islet cell tumors of the pancreas and oat cell carcinoma of the lung. The overwhelming majority of Cushing's syndrome cases in humans, however, trace their etiology to a pituitary adenoma. Symptoms of Cushing's syndrome include weight gain, central obesity, steroid hypersecretion, elevated urinary cortisol excretion, moon face, weakness, fatigue, backache, headache, impotence, mental status changes, muscle atrophy, and increased thirst and urination compared to mammals not suffering from this disease.

No medical therapies are currently available for Cushing's syndrome. In experienced specialized centers, surgical resection of ACTH-secreting pituitary microadenomas offers an overall cure rate of about 70–80%, but for macroadenomas control rates only approximate 30%, and the extensive surgical resection required portends significant risk to surrounding normal pituitary tissue, leading to partial or total hypopituitarism in about 80% of cases (Simmons, N. E., et al., Serum cortisol response to transphenoidal surgery for Cushing disease, J. Neurosurg. 95:1–8 [2001]; Mampalam, T. J., et al., Transsphenoidal microsurgery for Cushing's disease: A report of 216 cases, Ann. Intern. Med. 109:487–93 [1988]; Trainer, P. J., et al., Transsphenoidal resection in Cushing's disease: undetectable serum cortisol as the definition of successful treatment, Clin. Endocrinol. 38:73–8 [1993]).

Diagnosis and treatment of Cushing's syndrome remains a challenge (Oldfield, E. W., et al., Petrosal sinus sampling with and without corticotrophin-releasing hormone for the differential diagnosis of Cushing's syndrome, N. Engl. J. Med. 325:897–905 [1991]; Findling, J. W., et al., Diagnosis and differential diagnosis of Cushing's syndrome, Endocrinol. Metab. Clin. North Am., 30:729–47 [2001]; Orth, D. N., Cushing's syndrome, N. Engl. J. Med. 332:791–803 [1995). Therapy for patients harboring ACTH-secreting adenomas can be directed towards the hypothalamus, pituitary, or adrenal gland. Despite high resolution MR pituitary imaging, and petrosal sinus sampling to establish pituitary-derived ACTH hyper-secretion, pre-operative pituitary tumor localization and lateralization may be difficult (Oldfield, E. W., et al., Petrosal sinus sampling with and without corticotrophin-releasing hormone for the differential diagnosis of Cushing's syndrome, N. Engl. J. Med. 325:897–905 [1991]; Findling, J. W., et al., Diagnosis and differential diagnosis of Cushing's syndrome, Endocrinol. Metab. Clin. North Am., 30:729–47 [2001]). Although 70% of pituitary microaderiomas are successfully resected by transsphenoidal approaches, surgical "cure" rates for macroadenomas are achieved in only about a third of patients in specialized centers (Mampalam, T. J., et al., Transsphenoidal microsurgery for Cushing's disease: A report of 216 cases, Ann. Intern. Med. 109:487–93 [1988]). Post-surgical persistence of ACTH hypersecretion requires pituitary-directed radiation to suppress tumor growth and hormonal levels. Radiation effects may not be manifest for several years, and are ultimately associated with pituitary damage and dysfunction in most patients (Brada, M., et al., The long-term efficacy of conservative surgery and radiotherapy in the control of pituitary adenomas, Clin. Endocrinol. 38:571–8 [1993]). Hypercortisolism, cortisol hypersecretion, may be completely resolved by adrenalectomy (surgical removal of one or both of the adrenal glands), but this approach does not suppress pituitary tumor growth, and is also associated with other co-morbidity (Trainer, P. J., et al., Cushing's syndrome: Therapy directed at the adrenal glands, Endocrinol. Metab. Clin. North Am., 23:571–584 [1994]).

Medical therapy with cyproheptadine, an anti-serotonin agent, was used in the 1980's to suppress ACTH secretion but ultimate efficacy was poor, and its use has been discontinued (Krieger, D. T., et al., Cyproheptadine-induced remission of Cushings disease, N. Engl. J. Med. 293:893–6 [1975]). Although the antifungal, ketoconazole, suppresses adrenal cortisol biosynthesis, the drug does not inhibit pituitary tumor growth or ACTH secretion, and idiosyncratic hepatic impairment limits its longterm use (Sonino, N., The use of ketoconazole as an inhibitor of steroid production, N. Engl. J. Med. 317:812–8 [1987]).

Pituitary tumors and the many disease conditions associated therewith have not heretofore been associated with peroxisome proliferator-activated receptor gamma (PPAR-γ). PPAR-γ is a member of the nuclear receptor superfamily (Issemann, I., et al., Activation of a member of the steroid hormone receptor superfamily by peroxisome proliferators, Nature 347:645–660 [1990]; Schoonjans, K, et al., Peroxisome proliferator-activated receptors, orphans with ligands and functions, Curr. Opin. Lipidol. 8:159–166 [1997]), believed to function as a transcription factor mediating ligand-dependent transcriptional regulation (Kliewer, S. A., et al., Convergence of 9-cis retinoic acid and peroxisome proliferator signalling pathways through heterodimer formation of their receptors, Nature 358:771–774 [1992]; Palmer, C. A. N., et al., Interaction of the peroxisome proliferator-activated receptor alpha with the retinoid X receptor alpha unmasks a cryptic peroxisome proliferator response element that overlaps an ARP-1-binding site in the CYP4A6 promoter, J. Biol. Chem. 270:16114–16121 [1995]; Tontonoz, P., et al., MPPARy2: tissue-specific regulator of an adipocyte enhancer, Genes Dev. 8:1224–34 [1994]). High affinity PPAR-γ ligands include the insulin sensitizing thiazolidinedione compounds (TZD) (Spiegelman, B. M., PPAR-gamma: adipogenic regulator and thiazolidinedione receptor, Diabetes 47:507–514 [1998]; Kliewer, S. A., et al., A prostaglandin J2 metabolite binds peroxisome proliferator-activated receptor gamma and promotes adipocyte differentiation, Cell 83:813–819 [1995]; Forman, B. M., et al., 15-Deoxy-delta 12, 14-prostaglandin J1 is a ligand for the adipocyte determination factor PPAR gamma, Cell 83:803–812 [1995]). PPAR-γ activation leads to adipocyte differentiation (Spiegelman, B. M., PPAR-gamma: adipogenic regulator and thiazolidinedione receptor, Diabetes 47:507–514 [1998]), glucose regulation (Saltiel, A. R., et al., Thiazolidinediones in the treatment of insulin resistance and type II diabetes, Diabetes 45:1661–9 [1996]), and inhibition of macrophage and monocyte activation (Ricote, M., et al., The peroxisome proliferator-activated receptor-gamma is a negative regulator of macrophage activation, Nature 391:79–82 [1998]; Jiang, C., et al., PPAR-gamma agonists inhibit production of monocyte inflammatory cytokines, Nature 391:82–86 [1998]). PPAR-γ is expressed in breast, prostate and colon epithelium, and administration of synthetic PPAR-γ ligands inhibits prostate, and colon tumor cell growth (Staels, B., et al., Activation of human aortic smooth-muscle cells is inhibited by PPAR-alpha but not PPAR-gamma activators, Nature 393:790–793 [1998]; Elstner, E., et al., Ligands for peroxisome proliferator-activated receptor-γ and retinoic acid receptor inhibit growth and induce apoptosis of human breast cancer cells in vitro and in BNX mice. Proc. Natl. Acad. Sci. USA 95:8806–8811 [1998]; Kubota, T., et al., Ligand for peroxisome proliferator-activated receptor-γ (troglitazone) has potent anti-tumor effects against prostate cancer both in vitro and in vivo, Cancer Res. 58:3344–3352 [1998]; Sarraf, P., et al., Differentiation and reversal of malignant changes in colon cancer through PPAR gamma, Nat. Med. 4:1046–1052 [1998]), and anti-angiogenic actions of these ligands have also been demonstrated (Xin, X., et al., Peroxisome proliferator-activated receptor γ ligands are potent inhibitors of angiogenesis in vitro and in vivo, J. Biol. Chem. 274:9116–21 [1999]). In. U.S. Pat. No. 6,207,690, PPAR-γ ligands were implicated in the treatment of cancers and climacteric. (See also U.S. Pat. No. 5,814,647).

There remains a need for a non-invasive treatment of pituitary tumors, including effective drug therapies for hormone-secreting pituitary tumors such as Cushing's Syndrome. This and other benefits are provided by the present invention as described herein.

SUMMARY OF THE INVENTION

The present invention is based on the following discoveries: (1) that pituitary peroxisome proliferator-activated receptor gamma (also known as "peroxisome proliferating-activator receptor gamma" or "PPAR-γ") expression is restricted primarily to ACTH-secreting cells of the normal human anterior pituitary; (2) that pituitary PPAR-γ is abundantly expressed in human ACTH-, PRL-, LH-, GH-, and FSH-secreting pituitary tumors; (3) that PPAR-γ ligands potently inhibit ACTH-, PRL-, LH-, GH- secreting pituitary tumor proliferation in vitro, and inhibit pituitary tumor growth in vivo; and (4) that rosiglitazone, a known PPAR-γ ligand, administration suppresses 24 hour urinary cortisol excretion in Cushing's disease. These results support the role for PPAR-γ as a novel molecular target in the treatment of mammalian subjects afflicted with a pituitary tumor or Cushing's syndrome.

The present invention provides methods for treating pituitary tumors, including ACTH-secreting pituitary tumors, in a mammal. The inventive methods involve administering to the mammal having a pituitary tumor a therapeutically effective amount of PPAR-γ ligands. Such PPAR-γ ligands include thiazolidinediones (TZDs), such as troglitazone, pioglitazone, and rosiglitazone.

Another aspect of the present invention includes a method for preventing the formation of a pituitary tumor in a mammal, comprising administering to a mammal at higher than normal risk for developing a pituitary tumor an effective amount of at least one peroxisome proliferator activated receptor gamma ligand. A further aspect of the present invention includes a method for preventing the recurrence of a pituitary tumor in a mammal. The method involves administering to a mammal, said mammal previously having had a detectable pituitary tumor eliminated, an effective amount of at least one peroxisome proliferator activated receptor gamma ligand.

Yet another aspect of the present invention is a method for treating a mammal, including a human, exhibiting one or more symptoms of Cushing's syndrome (such as steroid hypersecretion and/or elevated urinary cortisol excretion) comprising administering to the subject a therapeutically effective amount of at least one PPAR-γ ligand.

The invention, together with various embodiments thereof, will be more fully explained by the accompanying drawings and the following detailed description of the preferred embodiments.

BRIEF DESCRIPTION OF THE DRAWINGS

FIG. 1 depicts an immunocytochemical analysis of autopsy-derived normal human pituitary tissue.

FIG. 2 depicts the results of a Western blot and immunocytochemical analysis, demonstrating abundant PPAR-γ expression in surgically resected human ACTH-secreting pituitary tumors. FIG. 2C further illustrates the results of the immunocytochemical analysis under higher magnification (magnification ×40), confirming PPAR-γ immunoreactivity, located in the cytoplasmic region of the corticotroph cells.

FIG. 3 depicts functional PPAR-γ in pituitary corticotroph tumors employing FACS analysis of troglitazone or rosiglitazone ($10^{-6}$ to $10^{-4}$ M) -treated mouse AtT20 cells and human ACTH-secreting corcticotroph pituitary tumor cells in vitro. FIG. 3D illustrates that rosiglitazone-treated murine AtT20 cells in vitro demonstrated a dose-dependent increase in Annexin-FITC immunoreactivity, a marker for apoptotic cells. The top portion of FIG. 3D is a graphic depiction of the observed dose dependent increase, represented as % apoptotic cells vs. rosiglitazone concentration, ranging from 0 to $10^{-4}$ M. The bottom portion of FIG. 3D, with panels marked a-f, shows cells treated with antibody to Annexin-FITC using green immunofluorescence (panels a-c), with panels d-f depicting the corresponding bright-field images, such that panel a corresponds with panel d, panel b corresponds with panel e, and panel c corresponds with panel f. Panels a and d depict cells treated with vehicle only; panels b and e depict cells treated with rosiglitazone $2\times10^{-5}$ M; and panels c and f depict cells treated with rosiglitazone $5\times10^{-5}$ M. Likewise.

FIG. 4A is a graphical summary of the results of an in vitro apoptosis study using TUNEL analysis, wherein a 2-fold increase in rosiglitazone-induced apoptosis was shown. (The bar designated "$ros^{-6}$" represents those cells treated with rosiglitazone $10^{-6}$ M; the bar designated "$ros^{-5}$" represents those cells treated with rosiglitazone $10^{-5}$ M; the bar designated "CRH" represents those cells treated with corticotrophin-releasing hormone (50 nM); and the bar designated "CRH & $ros^{-5}$" represents those cells treated both with rosiglitazone, $10^{-5}$ M, and CRH, 50 nM. FIG. 4B depicts an in vitro apoptosis study using TUNEL analysis wherein the upper panels (a,b,e, and f) depict AtT-20 cells using TRITC-staining and lower panel (c,d,g, and h) shows the corresponding bright-field images of the cells depicted in panels a,b,e, and f, respectively. FIG. 4B, panels a+c=control; panels b+d=Rosiglitazone $10^{-6}$ M, *=p=0.0003). Pre-treatment of the AtT20 cells with rosiglitazone blocked the anti-apoptotic effects of corticotrophin-releasing hormone (CRH), 50 nM, and induced corticotroph cell apoptosis (FIG. 4B, panels e+g), CRH 50 nM & ros $10^{-5}$ M (FIG. 4B, panels f+h), **, p=0.0003). Each bar represents mean ±SEM apoptotic cell number visualized in three distinct 10×microscopic fields in two separate experiments.

FIG. 5 depicts Western blot analysis showing reduced expression of the anti-apoptotic proteins and increased expression of pro-apoptotic proteins following rosiglitazone treatment of mouse corticotroph tumor cells.

FIG. 6 depicts a Northern blot analysis of TZD-treated corticotroph cell-derived total RNA extracts and rosiglitazone (ros) and Troglitazone (trog) and effects on baseline and CRH-induced (50 nM) POMC transcription.

FIG. 7 demonstrates rosiglitazone inhibition of corticotroph pituitary tumor growth in vivo. Following subcutaneous innoculation of corticotroph pituitary tumor cells (about 200,000 cells) into 4 week old female athymic nude mice, animals were randomized to receive either oral rosiglitazone (150 mg/kg/day) or vehicle.

FIG. 8 demonstrates that rosiglitazone-treatment slows growth of established pituitary corticotroph tumors and suppresses steroid hormone levels in vivo. Mice were inoculated subcutaneously with corticotroph pituitary tumor cells, and tumors were allowed to develop. By 3 weeks post-inoculation, all animals developed large visible tumors. The animals were randomized to receive either rosiglitazone (150 mg/kg/day) or vehicle orally. The results after further 3 weeks treatment are illustrated.

FIG. 9 demonstrates the effects of rosiglitazone treatment on cortisol excretion and pituitary corticotroph responsiveness.

FIG. 10 depicts the results of a Western blot and immunocytochemical analysis, demonstrating abundant PPAR-γ expression in surgically resected human non-functioning, GH-secreting, and PRL-secreting pituitary tumors.

FIG. 11 depicts functional PPAR-γ in pituitary tumors employing FACS analysis of rosiglitazone ($10^{-5}$ M) -treated pituitary cells in vitro and Northern and western blot analyses following rosiglitazone treatment. FIGS. 11A and 11B demonstrate increased $G_0$-$G_1$ phase and decreased S-phase in the rosiglitazone treated cells relative to the vehicle-treated control cells, *, p=0.001; **, p=0.03.

FIG. 12A, FIG. 12B, and FIG. 12C each illustrate the results of in vitro apoptosis studies using TUNEL analysis for cells receiving TZD treatment and control ("vehicle"), wherein the top panels represent cells viewed using bright-field images of the cells and the lower panels represent cells viewed using TRITC-staining. In FIG. 12A, TRITC-immunoreactive apoptotic rat GH3 somato-lactotroph cells were quantified. In the graph, the un-shaded bar represents the % of apoptotic cells observed for those cells treated with vehicle, while the shaded bar represents the % of apoptotic cells observed for those cells treated with troglitazone. In FIG. 12B, TRITC-immunoreactive apoptotic mouse gonadotroph cells are depicted following rosiglitazone treatment. In FIG. 12C, TRITC-immunoreactive apoptotic human pituitary tumor cells are depicted following rosiglitazone treatment. The results of the TUNEL analysis demonstrate TZD-mediated induction of apoptosis in mouse gonadotroph (alpha T3), rat somato-lactotroph (GH3), and human pituitary primary cultures (*, p=0.0002). 0.005% ethanol was used as vehicle.

FIG. 13 demonstrates rosiglitazone (ros) inhibition of somato-lactotroph pituitary tumor growth in vivo. Following subcutaneous inoculation of GH3 pituitary tumor cells. (about 200,000 cells) into 4 week old female athymic nude mice, animals were randomized to receive either oral rosiglitazone (150 mg/kg/day) or vehicle.

FIG. 14 demonstrates that rosiglitazone-treatment for 6 weeks inhibits pituitary gonadotroph tumor growth and suppresses LH hormone levels in vivo (n=5). Following subcutaneous inoculation of LBT2 LH-secreting gonadotroph pituitary tumor cells (about 200,000 cells) into nude mice, animals were randomized to receive either oral rosiglitazone (150 mg/kg/day) or vehicle.

FIG. 15 demonstrates that rosiglitazone-treatment slows growth of established pituitary gonadotroph tumors in vivo. Nude mice were inoculated subcutaneously with Alpha T3 gonadotroph pituitary tumor cells (about 200,000 cells), and tumors were allowed to develop. By 3 weeks post inoculation, all animals developed large visible tumors, such that tumor volumes were comparable in the vehicle and rosiglitazone-treated groups. The animals were randomized to receive either rosiglitazone (150 mg/kg/ day) (n=5) or vehicle (n=5) orally. The results after 6 weeks treatment following randomization are illustrated. At this milestone, the vehicle-treated control animals became debilitated, necessitating euthanitization.

DETAILED DESCRIPTION OF THE PREFERRED EMBODIMENTS

Figure 1A:
FIG. 1A and FIG. 1B each illustrate the immunocytochemical analysis using the immunoperoxidase method. In both FIG. 1A and FIG. 1B, ACTH immunoreactivity (dark regions, magnification ×10) was concentrated in the intermediate pituitary region.

The present invention relates to methods for treating a pituitary tumor in a mammal, for treating a Cushing's syndrome in a mammal, or for preventing the formation of a pituitary tumor in a mammal.

As used herein, the term "mammal" refers to warm-blooded vertebrate animals belonging to the class mammalia, including all that possess hair and suckle their young, e.g., human, non-human primates (e.g., apes and monkeys, such as baboons) rat, mouse, rabbit, monkey, baboon, bovine, porcine, ovine, canine, feline, and the like.

As used herein, the designation "pituitary tumor" or "pituitary adenoma" refers to non-cancerous growths that— depending on their specific location within the pituitary— can affect different hormone-producing regions of the gland. Pituitary tumors may lead to overproduction (hypersecretion) or underproduction (hyposecretion) of one of these hormones. Some examples of pituitary tumors that are associated with hormone hypersecretion are cortisol secreting tumors, ATCH secreting corticotrophic tumors, prolactinomas, and somatotrophic adenomas. In other instances, pituitary tumors are non-functional or "endocrine-inactive," meaning that they do not produce active hormones or produce an insufficient quantity of hormones to produce a clinical effect. Instead, they typically cause symptoms because of increasing size and pressure effect on the normal pituitary gland and on structures near the pituitary such as the optic nerves and chiasm. As these tumors enlarge, compression of normal pituitary glandular tissue can occur, resulting in decreased hormone production, pituitary failure (hypopituitarism), visual loss, and headache. As used herein, the designation "pituitary tumor" or "pituitary adenoma" also can include pituitary tumor cells or tissue grown or propagated in vitro. Also included within the meaning of these terms are pituitary tumor cells or tissue introduced into an in vivo animal model or transplanted to sites in said model other than the pituitary gland.

As used herein, the term "macroadenoma" refers to a pituitary adenoma in humans of one centimeter or larger in diameter. Pituitary macroadenomas are almost always benign in that they do not spread in any way, and thus are non-cancerous. They can, however, produce harm simply because of their location.

As used herein, the term "microadenoma" refers to a pituitary adenoma in humans of less than one centimeter in diameter. These tumors generally are too small to cause bone erosion or to put pressure on the optic chiasm. Unlike macroadenomas, they are too small to cause pressure-related symptoms, e.g., headache or visual field loss. Any morbidity is caused by excessive hormone secretion.

As used herein, the term "corticotrophic adenoma" refers to an ACTH-secreting pituitary tumor, typically found in the anterior lobe of the pituitary, usually measuring less than about 5 mm in diameter. The term "corticotrophic adenoma" also refers to an ACTH-secreting lung carcinoid, pancreatic carcinoid, thymic carcinoid. Corticotrophic adenomas are a recognized cause of Cushing's syndrome. Most pituitary ACTH-secreting adenomas (about 90%) are small in size (i.e., microadenomas).

Pituitary tumors in a mammalian subject can be detected using various means, depending on the tumor type. Hormone secreting pituitary tumors typically are detected by the subject presenting various physical abnormalities, e.g., caused by excessive hormone secretion (e.g., galactorrhea due to hyperprolactinemia, acromegaly due to excessive growth hormone, ACTH-mediated Cushing disease). Patients with prolactin-secreting adenomas may present, e.g., with infertility, galactorrhea, amenorrhea, and loss of libido. Growth hormone-secreting adenomas cause, e.g., acromegaly with coarsening of facial features and soft tissue swelling of the hands and feet. Most patients complain of excessive perspiration and offensive body odor. In some cases, progressive bony proliferation occurs, and the mandible lengthens and thickens, resulting in an underbite. ACTH-secreting adenomas cause Cushing disease characterized hereinbelow. If clinical suspicion of Cushing syndrome, acromegaly, or other hormone excess exists, a screening panel of circulating hormone levels, e.g., prolactin, can be measured for levels in excess of normal. In addition, MRI studies have shown sensitivity and specificity of about 90% for secretory tumors.

In non-functioning tumors, symptoms such as headache, visual loss, double vision, and/or pituitary failure may be manifest. Endocrine-inactive adenomas may also be detected incidentally during an evaluation for another problem, such as a head injury. Almost half of endocrine-inactive adenomas secrete part of a hormone called the alpha-subunit, which is not hormonally active but can be measured in the blood. An MRI of the pituitary without and with gadolinium (contrast agent) is the preferred study for visualizing a pituitary tumor. In most instances, a CT scan without and with contrast will also detect an adenoma.

As used herein, the term "treating," as it relates to the methods of the present invention, comprises administering a therapeutically effective amount of at least one PPAR-γ ligand to a mammal with a pituitary tumor. Included within the meaning of the term "treating" is reducing the size of the tumor tissue present in the pituitary, or eliminating the tumor tissue altogether such that no pituitary tumor tissue is detectable within the mammalian subject receiving the inventive treatment method. In accordance with the inventive method "reducing the size" of tumor tissue encompasses reducing the mass or weight, diameter, length, width, circumference, and/or the thickness or height, of the tumor tissue, and includes the elimination of the tumor tissue from the pituitary altogether.

Also included within the meaning of the word "treating" is the inhibition or arrest of tumor growth or size. Further included within the meaning of the word "treating" is the reversion of steroid levels to within the normal physiological range. Yet further included within the meaning of the word "treating" is improvement in one or more of the symptoms attendant a pituitary tumor, for example, hyper-secretion or hypo-secretion of hormones typically secreted by a healthy pituitary gland, including ACTH, PRL, GH, and LH.

Further included within the meaning of the word "treating" is administering a therapeutically effective amount of at least one PPAR-γ ligand to a mammal exhibiting one or more symptoms of Cushing's syndrome.

An "effective amount" is a dose sufficient to inhibit growth, reduce the size/eliminate, or prevent formation of pituitary tumor tissue or other detectable improvement in symptoms of attendant pituitary tumors, regardless of whether a pituitary tumor actually is detected. Such symptoms include pituitary gland hormone hyper- or hypo-secretion, and elevated urinary cortisol excretion. An "effective amount" also includes an amount effective for returning pituitary hormone secretion levels to within normal physiological range in the mammal relative to a control minus the PPAR-γ ligand. An "effective amount" for treating a human subject exhibiting one or more symptoms of Cushing's syndrome, e.g., steroid hypersecretion and/or elevated urinary cortisol excretion, is an amount sufficient to reverse, relieve, or ameliorate one or more of the symptoms of this condition.

The effective amount for each mammal will depend upon the particular PPAR-γ ligand selected. The effective amount for each mammal also will depend upon the particular size and individual physiology of the subject. The administered dose of PPAR-γ ligand should be adjusted as needed, based on prudent periodic monitoring of the mammal's condition by a skilled practitioner. In addition, the effective amount of active ingredient employed can vary depending on the mode of administration, the condition being treated, and the severity of the condition being treated. Thus, the effective amount can be ascertained readily by a person skilled in the art by routine screening tests. The skilled practitioner will readily apprehend that the screening tests appropriately employed to determine an effective amount or dose will depend on the individual clinical needs of each patient.

In the treatment of adult humans afflicted with a pituitary tumor or Cushing's syndrome, a preferred therapeutic dose range for administration of rosiglitazone, in accordance with the methods of the present invention, is between about 1and about 100 mg per day. The effective amount or dose is provided to the human subject in a single daily administration, or divided among two or more administrations per day. More preferably, the composition is formulated in a delivery system to deliver a dose of about 4 to about 20 mg of PPAR-γ ligands per day. This more preferred dose range provides the beneficial effect with essentially no toxic risk. This dosage regimen may be adjusted to provide the optimal therapeutic response. In the treatment of adult non-human mammals afflicted with a pituitary tumor or Cushing's syndrome, a preferred therapeutic range for administration of rosiglitazone, in accordance with the methods of the present invention, is between about 1 and about 300 mg/kg body mass daily. More preferably, the composition is formulated in a delivery system to deliver a dose of about 50 to about 150 mg/kg body mass daily. The effective amount for each subject will depend upon the physiologic reactions of the subject to whom the pharmaceutically acceptable compositions of the present invention are administered, and the subject's reactions will be monitored by the prescribing practitioner or physician.

Preventing the formation of pituitary tumors encompasses preventing the development of tumor tissue in the pituitary of a mammalian subject and/or preventing the development of symptoms attendant with a pituitary tumor, regardless of whether a detectable pituitary tumor actually is present, and particularly when none has been detected. The inventive method for preventing the formation of pituitary tumors is usefully applied to mammals, including humans, at higher than normal risk for developing pituitary tumors, relative to the general population. Examples of mammals at higher than normal risk include mammals already having had a detectable pituitary tumor eliminated, such as by having undergone tumor resection, chemotherapeutic, or radiotherapeutic treatment, such that the method is used to prevent recurrence of tumor growth.

Another example of mammals at higher than normal risk for developing pituitary tumors, relative to the general population, include mammals with a familial predisposition to developing a pituitary tumor. Examples of pituitary disorders that have been shown to exhibit a familial predisposition include, e.g., multiple endocrine neoplasia, Carney complex, and McCune Albright syndrome. (See Larsson, C., et. al., M. Multiple endocrine neoplasia type 1 gene maps to chromosome 11 and is lost in insulinoma, Nature 322:85–87 [1988]; Chandrasekharappak, S. C., et al., Positional cloning of the gene for multiple endocrine neoplasia- type 1, Science 276:404–406 [1997]; Stratakis, C. A., et al., Carney complex, familial multiple neoplasia and lentiginosis syndrome. Analysis of kindreds and linkage to the short arm of chromosome 2, J. of Clin. Invest. 97:699–705 [1996]; Lyons J., et al., Two G protein oncogenes in human endocrine tumors, Science 249:655–659 [1990]).

The inventive method of treating and method of preventing a pituitary tumor can be practiced to reduce or eliminate tumor growth, but also to simultaneously prevent formation of further tumors. The preceding is merely illustrative of factors that can contribute to a mammal being at higher than normal risk of developing pituitary tumors, and is not an exhaustive list.

As used herein, the term "Adrenocorticotrophic Hormone" (ACTH) means the peptide hormone produced by the anterior pituitary gland that stimulates the adrenal cortex to secrete glucocorticoid hormones, which help cells synthesize glucose, catabolize proteins, mobilize free fatty acids and inhibit inflammation in allergic responses. One such hormone is cortisol, which regulates metabolism of carbohydrate, fat, and protein metabolism.

Prolactin (PRL) is produced from the anterior pituitary gland, and is found in the serum of normal females and males. It is known as a gonadotrophic hormone as it affects the gonads (testes and ovaries). It also has an effect on other organs in the body. In males, prolactin influences the production of testosterone and affects sperm production. Prolactin's principal physiological action in women is to initiate and sustain lactation.

Growth hormone (GH), also known as somatotropin, is a protein hormone of about 190 amino acids that is synthesized and secreted by cells called somatotrophs in the anterior pituitary. It is a major participant in control of several complex physiologic processes, including growth and metabolism. The major role of growth hormone in stimulating body growth is to stimulate the liver and other tissues to secrete IGF-1. Growth hormone also has important effects on protein, lipid and carbohydrate metabolism.

As used herein, "Luteinizing Hormone" (LH) means the peptide hormone secreted from cells in the anterior pituitary called gonadotrophs. The effects of LH also depend on sex. LH is known as a gonadotropin because it stimulates the gonads—in males, the testes, and in females, the ovaries. In sexually-mature females, LH stimulates the follicle to secrete estrogen in the first half of the menstrual cycle a surge of LH triggers ovulation in the middle of the cycle, and stimulates the secretion of progesterone during the latter half of the menstrual cycle. In males, LH acts on the interstitial cells of the testes stimulating them to synthesize and secrete the male sex hormone, testosterone.

For purposes of the present invention a useful peroxisome proliferator-activated receptor gamma (PPAR-γ) ligand is a compound that activates PPAR-γ or otherwise acts as a PPAR-γ agonist, whether such compounds are now known, or later developed or discovered. Some of these known compounds and methods for making them are disclosed in, e.g., WO 91/07107; WO 92/02520; WO 94/01433; WO 89/08651; JP Kokai 69383/92; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; 5,260,445; 5,814,647, and 6,200,998.

The PPAR-gamma ligands may be obtained commercially. Alternatively, they are synthesized from commercially available precursors, and/or purified or isolated from naturally occurring sources by known biochemical means. (See, e.g., U.S. Pat. No. 6,200,998). Synthetic or semisynthetic versions or derivatives of PPAR-γ ligands are also useful in the inventive method, as are pharmaceutically acceptable salts of PPAR-γ ligand compounds associated with various anions and cations, including, for example, succinate, glutamate, maleate, fumarate, sodium, magnesium, calcium, hydrochloride, chloride, sulfate, carbonate, or bicarbonate. Compounds useful for practicing the present invention include, without limitation, thiazolidinediones and other compounds which have the molecular motif of an aryl group attached to the 5-position of thiazolidinedione (TZD) backbone.

Useful PPAR-γ ligands are thiazolidinedione compounds (TZDs), including rosiglitazone, pioglitazone, and troglitazone. In one preferred embodiment, the PPAR-γ ligand is rosiglitazone, commercially sold in the form of rosiglitazone maleate, also known as (±)-5-[[4-[2-(methyl-2-pyridinylamino)ethoxy]phenyl]methyl]-2,4-thiazolidinedione,(Z)-2-butenedioate, having the chemical formula $C_{18}H_{19}N_3O_3S \cdot C_4H_4O_4$. Rosiglitazone is a potent thiazolinedione oral antidiabetic agent, which recently was approved in the U.S. by the FDA for administration to human subjects. Rosiglitazone has greater PPAR-γ binding affinity and antihyperglycaemic potency than pioglitazone and troglitazone (other approved thiazolidinediones). Troglitazone is also known as (±)-5-[4[(6-Hydroxy-2,5,7,8-tetramethylchroman-2-yl)methoxy]-benzyl]-2,4-thiazolidinedione, having the molecular formula $C_{24}H_{27}NO_5S$. Pioglitazone, commonly sold as pioglitazone hydrochloride, is also known as [(±)-5-[[4-[2-(5-ethyl-2pyridinyl)ethoxy]phenyl]methyl]-2,4-]thiazolidinedione mono-hydrochloride, having the molecular formula $C_{19}H_{20}N_2O_3S \cdot HCl1$.

Clinical surveillance of more than 4500 patients show that rosiglitazone is a safe, effective mono- or combination therapy for human patients with type 2 diabetes (Goldstein, B. J., Rosiglitazone, Int. J. Clin. Pract. 54:333–7 [2000]). Similarly, pioglitazone is used as a treatment for type 2 diabetes and received FDA approval on Jul.16, 1999. Troglitazone was introduced into the market in January, 1997 and withdrawn from the market in March, 2000 due to reports of liver toxicity in humans and its use should be monitored with particular caution by the practitioner as to patient responses.

The present invention is not committed to, or dependent upon, any particular mechanism by which the PPAR-γ ligand operates to reduce the size of, or inhibit or prevent the growth or development of, or treat the symptoms of pituitary tumors in a mammal. Regardless, several mechanisms have been proposed for TZD-induced cell-cycle arrest, including preventing Rb phosphorylation by inhibiting cyclin D1-kinase activity, increased p21 (CiP) or p27 (Kip) expression. (Wakino, S., et al., Peroxisome proliferator-activated receptor γ ligands inhibit retinoblastoma phosphorylation and G1→S transition in vascular smooth cells, J. Biol. Chem. 275:22435–41 [2000]); Sugimura, A., et al., Troglitazone suppresses cell growth of myeloid leukemia cell lines by induction of p21WAF1/CIP1 cyclin-dependent kinase inhibitor, Biochem. Biophys. Res. Comm. 261:833–7 [1999]; Motomura, W., et al., Activation of peroxisome proliferator-activated receptor gamma by troglitazone inhibits cell growth through the increase of p27KiP1 in human pancreastic carcinoma cells, Cancer Res. 60:5558–64 [2000]).

Candidate molecules which mediate TZD-induced apoptosis include reduced Bcl-2, and increased Bax and TRAIL (Goke, R., et al., Regulation of TRAIL-induced apoptosis by transcription factors, Cell. Immunol. 201:77–81 [2000]; Staels, B., et al., Activation of human aortic smooth-muscle cells is inhibited by PPAR-alpha but not PPAR-gamma activators, Nature 393:790–793 [1998]).

PPAR-γ ligand(s) can be administered, in accordance with the methods of the present invention, in pharmaceutically acceptable compositions. "Administering" includes giving, providing, feeding, dispensing, inserting, injecting, infusing, perfusing, prescribing, furnishing, treating with, taking, spraying, inhaling, swallowing, eating or applying a pharmaceutically acceptable PPAR-γ ligand-containing composition.

Any suitable delivery route can be employed for providing a mammal with an effective dosage of a PPAR-γ ligand. Preferred delivery routes for the PPAR-γ ligands effectively transport the active compound to the appropriate or desired site of action. Such delivery routes are well known to those of skill in the art and include, but are not limited to, oral, ocular, pulmonary, transdermal, transmembranal, or parenteral, e.g., rectal, topical, subcutaneous, intravenous, intraurethral, intramuscular, intranasal (nose drops or spray), inhaler, ophthalmic solution or an ointment, the oral delivery route being preferred.

PPAR-γ ligands can be in any dosage form suitable for administration to a mammal. Dosage forms include tablets, troches, lozenges, hard or soft capsules, caplets, microspheres, dispersions, suspensions, solutions, aerosols, dispersible powders or granules, syrups, elixirs, enteral formulas, ointments, or other topical applications, and the-like.

As well as the PPAR-γ ligands, the pharmaceutically acceptable compositions for use in accordance with the methods of the present invention can optionally contain pharmaceutically acceptable solvent(s), adjuvant(s) and/or pharmaceutically acceptable non-medicinal, non-toxic carrier(s), binder(s), thickener(s), and/or filler substance(s) that are known to the skilled artisan for the formulation of tablets, pellets, capsules, solutions, emulsions, suspensions, and any other form suitable for use. The carriers which can be used include, without limitation, glucose, lactose, sucrose, gum acacia, gelatin, mannitol, starch, starch paste, magnesium trisilicate, talc, corn starch, keratin, colloidal silica, potato starch, urea, medium chain length triglycerides, dextrans; and other carriers suitable for use in manufacturing preparations, in solid, semisolid, or liquid form. In addition, auxiliary, stabilizing, thickening and coloring agents and perfumes can be used. Also contemplated are additional medicinal or nutritive additives in combination with at least one PPAR-γ ligand, as may be desired to suit the more particular needs of the practitioner.

By way of example, if a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution. Compositions can also be coated by known techniques, e.g., as described in the U.S. Pat. Nos. 4,256,108; 4,160,452; and 4,265,874, to form osmotic therapeutic tablets for controlled release. Other exemplary techniques for controlled release compositions, such as those described in the U.S. Pat. Nos. 4,193,985; and 4,690,822; 4,572,833 also can be used in the formulation of the pharmaceutically acceptable compositions of the inventive method.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

For intranasal or inhalant administration, the preparation can contain PPAR-γ ligands dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

The pharmaceutically acceptable composition can be formulated and manufactured at more than one concentration unit of PPAR-γ ligand, such that modular incremental amounts of PPAR-γ ligands are easily administered.

The pharmaceutically acceptable compositions in accordance with the method of the present invention can be formulated and manufactured at more than one concentration of PPAR-γ ligand, such that modular increments of PPAR-γ ligand can be easily administered within the preferred dose range for the particular mammal. In general, the preferred effective dose range of PPAR-γ ligands, in accordance with the preferred method, is well below toxic levels.

Where the PPAR-γ ligand, for example, is either rosiglitazone or troglitazone, used in connection with the treatment of diabetic-related conditions in humans, troglitazone, is administered preferably in 10-fold higher doses, than is rosiglitazone. About 20 milligrams per day of rosiglitazone has been administered to humans for sustained periods of time without adverse effects.

In the treatment of adult humans afflicted with a pituitary tumor or Cushing's syndrome, a preferred therapeutic dose range for administration of rosiglitazone, in accordance with the methods of the present invention, is between about 1 and about 100 mg per day. The effective amount or dose is provided to the human subject in a single daily administration, or divided among two or more administrations per day. More preferably, the composition is formulated in a delivery system to deliver a dose of about 4 to about 20 mg of PPAR-γ ligands per day. This more preferred dose range provides the beneficial effect with essentially no toxic risk. This dosage regimen may be adjusted to provide the optimal therapeutic response.

In the treatment of adult non-human mammals afflicted with a pituitary tumor or Cushing's syndrome, a preferred therapeutic range, for administration of rosiglitazone, in accordance with the methods of the present invention, is between about 1 and about 300 mg/kg body mass daily. More preferably, the composition is formulated in a delivery system to deliver a dose of about 50 to about 150 mg/kg body mass daily.

In accordance with the inventive methods, administration of PPAR-γ ligands can be of short duration or can be continued indefinitely as needed. The duration of administration of the method of the present invention varies with the particular pituitary condition sought to be treated. For example, in a subject afflicted with a pituitary tumor, treatment typically will continue until the tumor is no longer detectable in the subject. On the other hand, where the subject is at high risk for recurrence of a pituitary tumor, preventive treatment can proceed even after the time at which no tumor is detectable. In other cases, PPAR-γ ligands can be administered until the subject's steroid levels revert to within the normal physiological range.

In accordance with the inventive methods, PPAR-γ ligands can be administered alone or in combination with other drugs that may also be useful in the treatment, prevention, suppression or amelioration of the diseases or conditions for which they are useful. Such other drugs may be administered, by a route and in an amount commonly used therefor, contemporaneously or sequentially with said PPAR-γ ligands. When a PPAR-γ ligand is used contemporaneously with one or more other drugs, a pharmaceutical composition in unit dosage form containing such other drugs and the PPAR-γ ligands is preferred. It is also contemplated that when used in combination with one or more other active ingredients, PPAR-γ ligands and the other active ingredients can be used in lower doses than when each is used singly.

Examples of such other drugs that can be combined with PPAR-γ ligands in accordance with the present invention, either administered separately or in the same pharmaceutical compositions, include, but are limited to: somatastatin, somatostatin analogs such as Octreotide, retinoic acid, retinoic acid receptor (RAR) and RAR-like ligands, Ketoconazole, Metyrapone, and dopamine agonists such as bromocriptine.

The invention now will be described in greater detail by reference to the following examples. These examples are not to be construed in any way as limiting the scope of this invention.

EXAMPLE 1

Materials and Methods

Patients and Tissues. Surgically resected ACTH-secreting pituitary adenoma samples were obtained from six consecutive unselected patients after surgical resection, in accordance with institutional guidelines. For primary human pituitary cultures, pituitary tumor tissue, freshly obtained at surgery was minced mechanically and digested for 45 minutes at 37° C. with 0.35% collagenase, and 0.1% hyaluronidase (Sigma Co., St. Louis, Mo.) in 10 mL DMEM medium. Cell suspensions were filtered and resuspended for 24 hours in low glucose DMEM containing 10% FBS, 2 mM glutamine and antibiotics (such as penicillin, streptomycin, and fungazone), prior to treatment with vehicle or rosiglitazone.

Cell Culture. Subconfluent AtT20 mouse pituitary (ACTH-secreting) tumor cells were cultured in DMEM medium (Gibco BRL, Grand Island, N.Y.) supplemented with 10% fetal calf serum (FCS) and antibiotics at 37° C. in 5% $CO_2$ for 24 hours prior to treatment with troglitazone or rosiglitazone, as the case may be. Medium was replenished with ligands every 2 days, and cells maintained in serum-containing medium or in serum-free medium for up to 96 hours.

Cell Cycle Distribution. Following treatments, AtT20 cells were trypsinized, centrifuged (1500 rpm×2 min), washed with PBS, and treated with 20 g/mL Rnase A (Calbiochem, La Jolla, Calif.). DNA was stained with 100 μg/mL propidium iodide (PI) for 30 min at 40° C. and protected from light, prior to analysis with a FACScan (Becton Dickinson, Franklin Lakes, N.J.). DNA histogram analysis was performed using the modFitLT software.

Apoptosis Assay. Annexin FITC by flow Cytometry. AtT20 cells were treated, washed in PBS, trypsinized, centrifuged, and washed prior to incubation with a FITC-labelled monoclonal Annexin antibody and PI for 30 min at room temperature according to manufacturer's instructions (Pharmingen, San Diego, Cailf.). About $1\times10^6$ cells were prepared and analyzed by flow cytometry, labeled nuclei (PI) were gated on light scatter to remove debris, and the percentage of Annexin-FITC positive cells was determined. Annexin-FITC positive cells were also visualized with an Olympus BH2 immunofluorescent microscope.

Terminal Deoxynucleotidyltransferase-mediated dUTP Nick End Labeling (TUNEL). Apoptosis-induced nuclear DNA fragmentation was detected using the in situ cell death detection kit, TMR red (Roche Diagnostics, Indianapolis, IN) following the manufacturer's protocol. Briefly, 48 hours following treatment with thiazolidinedione compounds (TZDs), AtT20 cells were fixed in 4% paraformaldehyde, permeabilized with 0.1% sodium citrate/ 0.6% Tween 20 (pH 7.4) for 2 min at 4° C. prior to incubation in Tunel reaction mix (TMR red/dNTP mix, TdT, and labeling buffer) for 60 min at 37° C. Slides were washed (3×5 min) in PBS/ Triton/ BSA (0.3%) and visualized on an Olympus BH2 immunofluorescent microscope.

Transfection with POMC promoter. Following incubation in serum-replete medium with/without rosiglitazone ($10^{-5}$ M) for 48 hours, a POMC promoter reporter construct (−706/+64 rat POMC-luc), kindly provided by Dr. Malcolm Low, Vollum Institute, Oregon (Hammer, G. D., et al., Pituitary-specific and hormonally regulated gene expression directed by the rat proopiomelanocortin promoter in transgenic mice, Mol. Endocrinol. 4:1689–97 [1990]) was transiently transfected into AtT20 cells using Lipofectamine 2000 (Gibco BRL). Cells were then incubated with rosiglitazone or corticotrophic releasing hormone (CRH, 50 nM) as described (Auernhammer, C. J., et al., Interleukin-11 stimulates proopiomelanocortin gene expression and adrenocorticotrophin secretion in corticotroph cells: evidence for a redundant cytokine network in the hypothalmo-pituitary-adrenal axis, Endocrinology 140:1559–66 [1999]).

Northern blot analysis. Total RNA was extracted from cell cultures (about $3\times10^7$ cells/group) or from excised tissues with TRIzol (Gibco). Rat testis RNA served as a positive control for PTTG expression. Electrophoresed RNA was transferred to Hybond-n nylon membranes (Amersham International, Buckinghamshire, UK), and hybridized as previously described (Heaney, A. P., et al., Estrogen induced Pituitary Tumor Transforming Gene (PTTG) and bFGF in Pituitary Tumor Pathogenesis, Nature Medicine 5:1317–1321 [1999]).

Immunocytochemical studies of pituitary glands. Surgically excised human pituitary tumor and normal pituitary autopsy tissues were obtained in accordance with institutional review board guidelines. Pituitary tissues from vehicle-or TZD-treated mice were obtained in accordance with institutional animal care and use committee guidelines. All tissues were fixed in 4% paraformaldehyde and processed for paraffin embeddment. Sections were immunostained using antibodies to human or mouse ACTH (1:1000) (DAKO, Carpinteria, Cailf.), PPAR-γ (1:500) (Calbiochem, La Jolla, Cailf.) using both the avidin-biotin-peroxidase method, and avidin-biotin-FITC and TRITC for double immunostaining, and counter-stained with haematoxylin. Negative controls were performed for each slide, using pre-adsorbed or non-immune serum.

Western Blot Analysis: AtT20 cells were seeded at about $1\times10^6$ per well and human pituitary cell cultures were seeded at about $0.5\times10^6$ per well in 6-well plates for 24 hours prior to treatment with TZD's. Cells were then washed with PBS, and protein samples prepared in RIPA buffer and resolved under reducing conditions on 12% SDS-polyacrylamide gels using standard methods (Elstner, E., et al., Ligands for peroxisome proliferator-activated receptor-γ and retinoic acid receptor inhibit growth and induce apoptosis of human breast cancer cells in vitro and in BNX mice. Proc. Natl. Acad. Sci. USA 95:8806–8811 [1998]). Resolved proteins were transferred to nitrocellulose membranes and probed with antibodies to Bcl-2 (1:500), Bax (1:1000), TRAIL (1:500), p53 (1:1000) (all from Santa-Cruz, Cailf.), p-Rb (Ser 795) (1:1000), cleaved and uncleaved caspase-3 (1:500) (Cell Signalling, Beverly, Mass.) overnight at 4° C. After washing, membranes were incubated with appropriate IgG- horseradish peroxidase conjugates, and immunoreactive protein bands were visualized with ECL (Amersham, Buckinghamshire, UK). Total protein was normalized by reprobing with anti-actin antibody (1:5000, Sigma, St. Louis, Mo.) or Ponceau S staining, and protein bands quantified by densitometry (Video Densitometer model 620, Bio-Rad).

EXAMPLE 2

Results

PPAR-γ is Selectively Expressed in Pituitary Corticotroph Cells

Figure 1B:
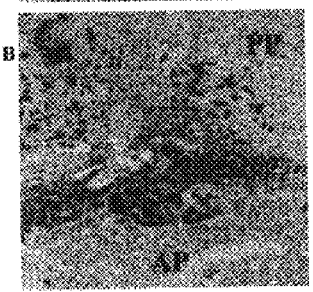
Figure 1C:
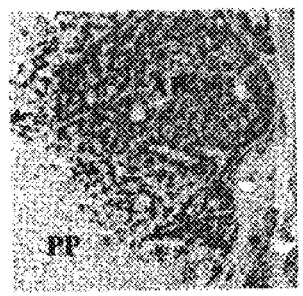
FIG. 1C and FIG. 1D also illustrate the immunocytochemical analysis using the immunoperoxidase method. PPAR-γ immunoreactivity (dark regions, magnification ×10) also was observed in the intermediate region of the pituitary, and appeared to be localized in the ACTH-immunoreactive pituitary cells.
Figure 1D:
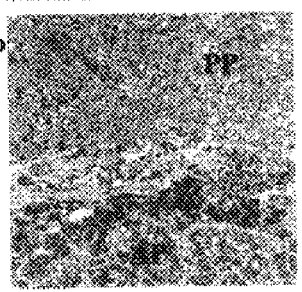
Figure 1E:
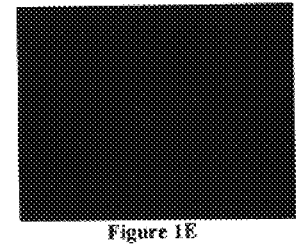
FIG. 1E and FIG. 1F illustrate anterior pituitary double immunofluorescence using TRITC-labeled ACTH (FIG. 1E) and using FITC-labeled PPAR-γ antibodies (FIG. 1F).
Figure 1F:
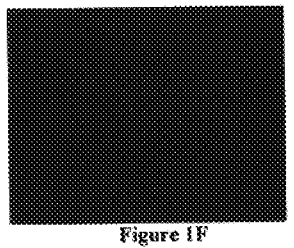
Figure 1G:
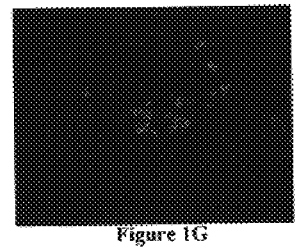
FIG. 1G shows a superimposition of the images from FIG. 1E and FIG. 1F and depicts co-localization of PPAR-γ and ACTH-immunoreactivity (magnification ×40). The pituitary is composed of 2 parts, the anterior pituitary, designated "AP," and the posterior pituitary, designated "PP".

Immunocytochemical analysis of post mortem-derived normal human pituitary tissue, using the avidin-biotin-peroxidase method or TRITC-labeled ACTH and FITC-labeled PPAR-γ antibodies demonstrated characteristic diffuse ACTH immunoreactive cells throughout the anterior pituitary in about 15% of cells, but concentrated in the intermediate region between the anterior and posterior pituitary (FIG. 1A and FIG. 1B). PPAR-γ-FITC immunoreactivity was exclusively present in cells located in the intermediate region of the pituitary (FIG. 1C and FIG. 1D). Double immunofluorescence studies using TRITC-labeled and FITC-labeled antibodies revealed that all PPAR-γ immunoreactive cells co-localized with ACTH-immunoreactive cells (FIG. 1E, FIG. 1F, and FIG. 1G). Striking basophil (corticotroph) invasion into the posterior pituitary of the PPAR-γ/ACTH-immunoreactive cell population was evident (See, e.g., FIG. 1C).

PPAR-γ is Expressed in ACTH-secreting Pituitary Tumors

Figure 2A:
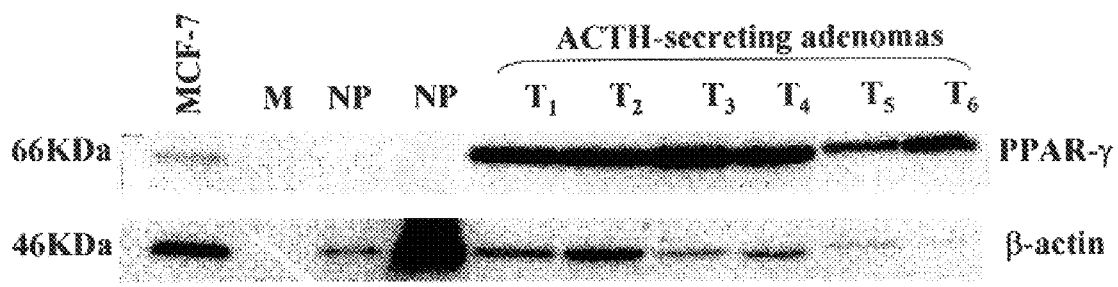
FIG. 2A, upper panel, demonstrates the results of a Western blot of 6 surgically resected ACTH-secreting pituitary tumors ($T_{1-6}$), in comparison to PPAR-γ expression in two normal pituitary tissue-derived extracts (NP). β-actin immunoblotting confirmed equivalent total protein loading (FIG. 2A, lower panel). MCF-7 breast cancer cells served as a positive control, and M served as a protein marker (Amersham molecular weight protein marker).
Figure 2B:
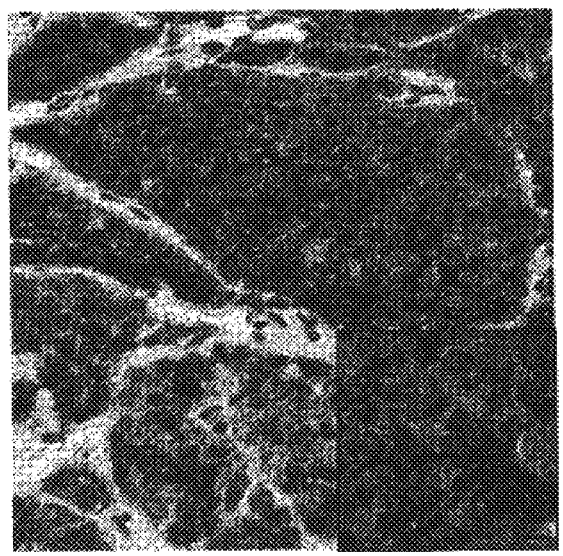
FIG. 2B depicts the results of the PPAR-γ immunocytochemical analysis of the surgically resected ACTH-secreting pituitary tumor tissue (magnification ×10).

Given the observed co-localization of PPAR-γ and ACTH in normal human anterior pituitary corticotroph cells, PPAR-γ expression was assessed in 6 consecutive surgically resected ACTH-secreting human pituitary tumor specimens. Western blotting of pituitary tumor-derived protein extracts revealed abundant PPAR-γ expression in all six ACTH-secreting pituitary tumors examined, in comparison to modest PPAR-γ expression in two normal pituitary-derived extracts (FIG. 2A). Immunocytochemical analysis of the resected tissue demonstrated: abundant PPAR-γ immunoreactivity localized to those pituitary adenoma cells which also expressed ACTH (FIG. 2B and FIG. 2C).

Functional Role for Pituitary PPAR-γ Receptor in Vitro

Figure 3A:
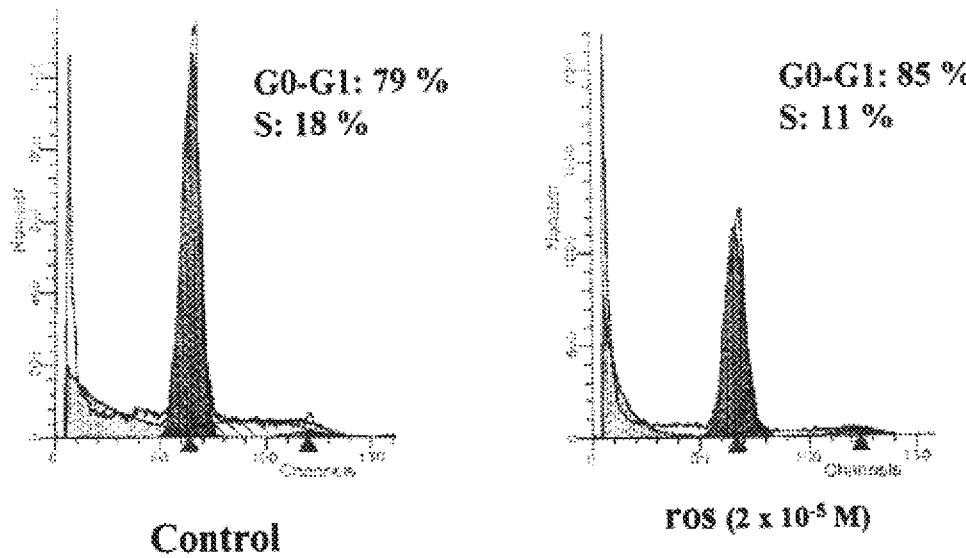
FIG. 3A illustrates that a greater proportion of the rosiglitagene-treated mouse AtT20 cells were in $G_0$-$G_1$ phase relative to vehicle-treated control cells.
Figure 3B:
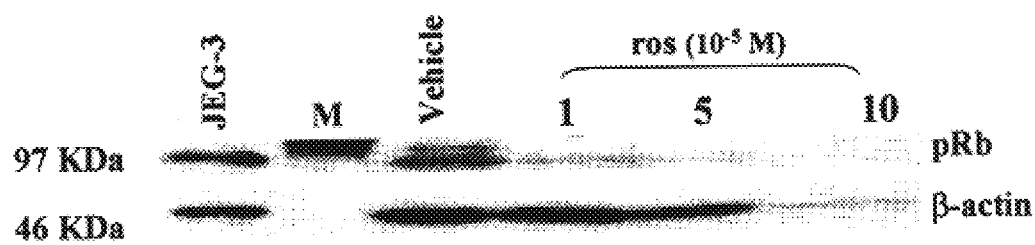
FIG. 3B illustrates that the mouse AtT20 cells demonstrated decreased expression of $Ser^{794}$ phosphorylated retinoblastoma protein relative to vehicle-treated cells. (JEG-3 choriocarcinoma cells served as a positive control, M represents protein marker).
Figure 3C:
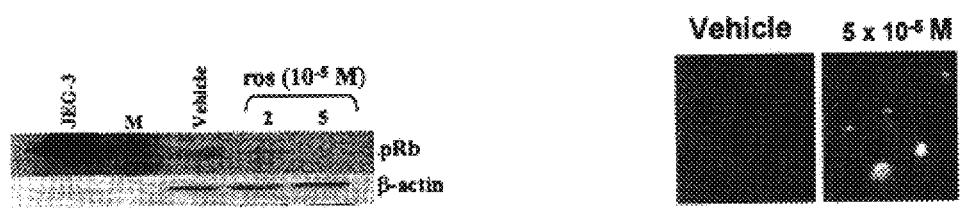
FIG. 3C illustrates a dose-dependent decrease in phosphorylated retinoblastoma protein in human ACTH-secreting pituitary corticotroph tumor cells in vitro, in keeping with the observed thiazolidinedione compounds (TZD)-mediated induction of G1 cell-cycle arrest.

To determine the functional significance of pituitary corticotroph PPAR-γ expression, the effects of PPAR-γ ligands were tested on ACTH-secreting pituitary tumor cells in vitro. Troglitazone or rosiglitazone-treatment ($10^{-6}$ to $10^{-4}$ M) for up to 48 hours, when cells were maintained in serum-free conditions, or up to 96 hours, when cells were maintained in serum-replete conditions, induced $G_0$–$G_1$ cell-cycle arrest (control, $G_1$ 75±4% vs. ros, $G_1$ 85±2%, p=0.009), and led to decreased S-phase cells (control, 18±0.05% vs. ros, 12±0.5%, p=0.001) (FIG. 3A). Western blot analysis of protein extracts derived from TZD-treated corticotroph cells showed an about 60% decrease in $Ser^{795}$ phosphorylated retinoblastoma protein expression (FIGS. 3B and 3C), indicating a mechanism for the observed $G_0/G_1$ cell-cycle arrest, indicating the functional significance of the observed corticotroph tumor PPAR-γ expression.

Figure 3E:
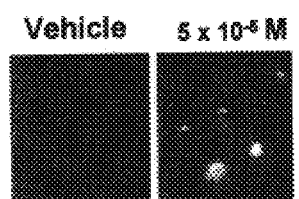
FIG. 3E illustrates that human ACTH-secreting pituitary corticotroph tumor cells in vitro demonstrated an increase in Annexin-FITC immunoreactivity in rosiglitazone treated cells versus vehicle treated cells.
Figure 4:
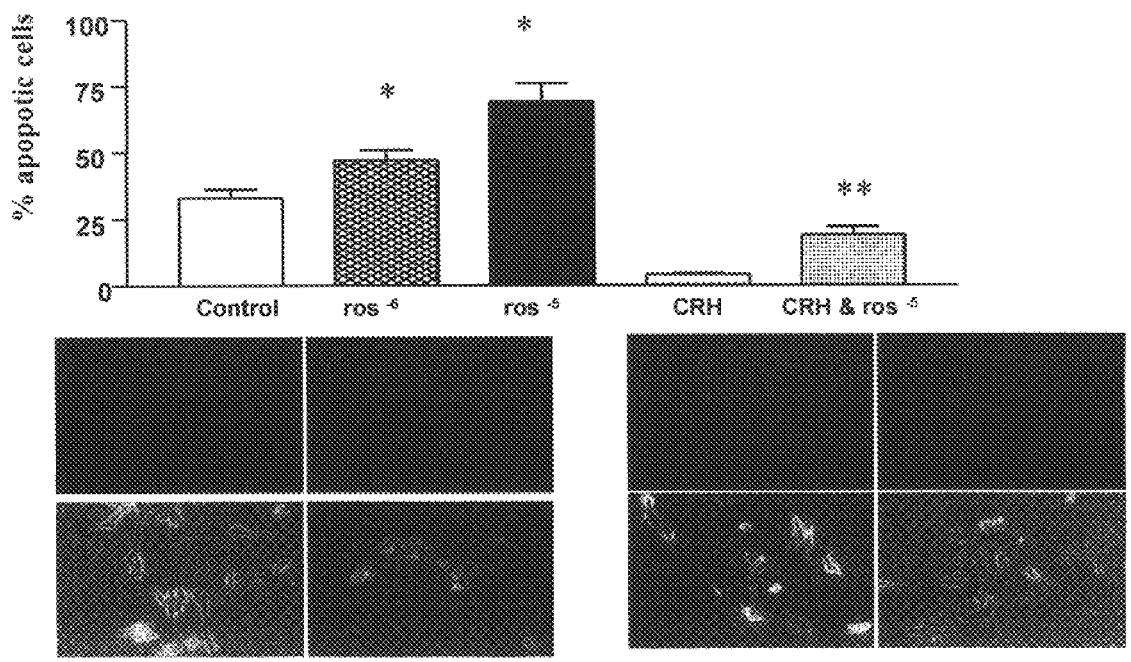
FIG. 4 illustrates that treatment with TZDs induced cell death and apoptosis in AtT-20 cells.

Rosiglitazone ($10^{-5}$ to $10^{-4}$ M) treatment of AtT20 cells for 48 hours demonstrated a dose-dependent increase in Annexin-FITC immunoreactive AtT20 cells, and enhanced apoptosis (FIG. 3D, p<0.001). A similar increase in Annexin-FITC immunoreactive cells was observed after treatment of human pituitary corticotroph tumor cultures with rosiglitazone ($10^{-5}$ M) (FIG. 3E). TUNEL analysis confirmed that TZD-induced cell death, and increased apoptosis by about 3-fold (FIG. 4A and FIG. 4B, a-d) (% apoptosis: Control, 33±3% vs. ros, $10^{-6}$ M 47±4%; ros, $10^{-5}$ M 69±7%, p<0.001). Corticotrophin releasing hormone (CRH) is a potent corticotroph proliferative factor (FIG. 4B, e+g) (Vale W., et al., Characterization of a 41-residue ovine hypothalamic peptide that stimulates secretion of corticotropin and beta-endorphin, Science 213:139–47 [1981]). Pre-treatment of AtT20 cells with TZD prior to CRH (50–100 nM) blocked the growth-promoting effects of CRH (50 nM for 24 hours) and induced corticotroph cell apoptosis (FIG. 4B, f+h) (% apoptosis; CRH 50 nM, 4±0.5% vs CRH & ros $10^{-5}$ M 19±3%, p<0.05).

Figure 5A:
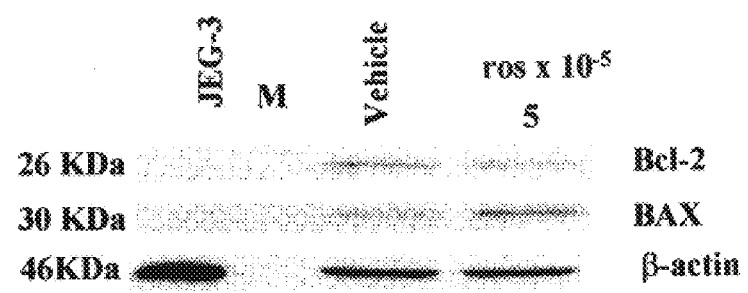
FIG. 5A shows reduced expression of the anti-apoptotic protein Bcl-2 (upper panel) and increased expression of pro-apoptotic protein BAX (middle panel). β-actin (lower panel) serves as an internal standard for protein loading.
Figure 5B:
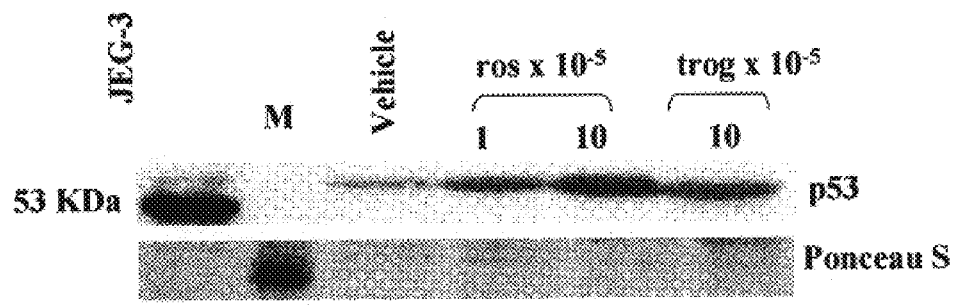
FIG. 5B shows increased expression of pro-apoptotic protein p53 in rosiglitazone (ros) and Troglitazone (trog) treatments (both at $10^{-5}$ M), relative to vehicle-treated control cells. Ponceau S is a protein dye.
Figure 5C:
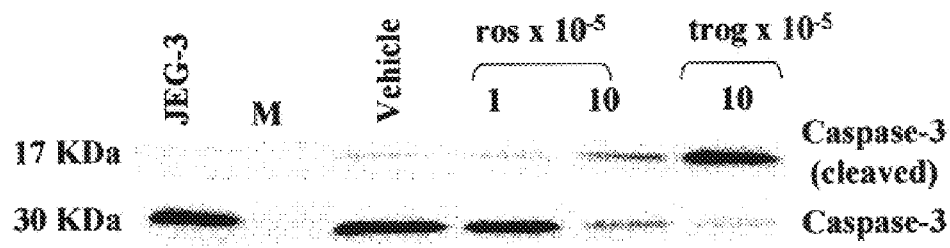
FIG. 5C illustrates a dose-dependent increase in TZD-mediated cleavage of Caspase-3 ("cleaved"; upper panel) and a concordant decrease in uncleaved caspase-3 (lower panel). JEG-3 choriocarcinoma cells served as a positive control, M represents protein marker.

Western blot analysis of protein extracts derived from TZD-treated mouse corticotroph cells showed decreased expression of the anti-apoptotic protein Bcl-2, and increased levels of pro-apoptotic Bax and p53 expression suggesting a potential mechanism for the observed increased apoptosis (FIG. 5A and FIG. 5B). An about 4-fold increase in cleaved caspase-3 and a concomitant decrease in total caspase-3 resulted from TZD-treatment, and were consistent with enhanced apoptosis (FIG. 5C). Capsase-3 is an enzyme involved in the later stages of cell apoptosis, whose enzymatic-activity is activated after having been cleaved.

PPAR-γ Ligands Inhibit ACTH and PTTG mRNA Expression and POMC Transcription

Figure 6A:
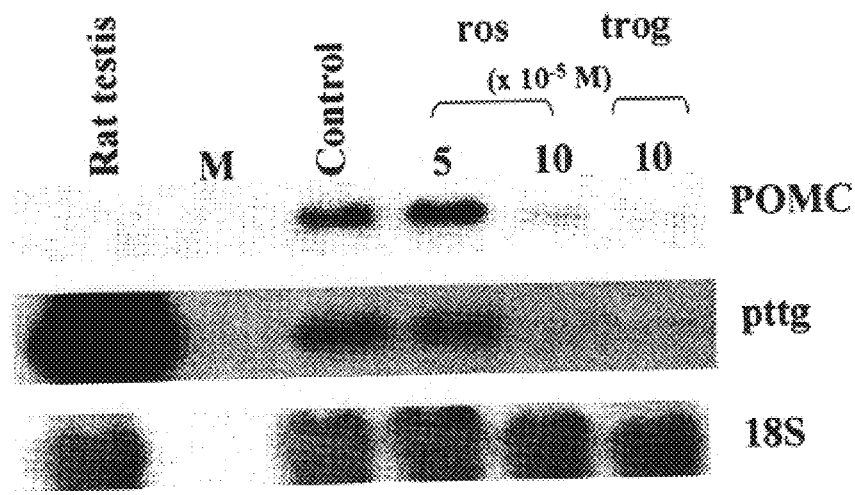
In FIG. 6A, the Northern blot analysis of TZD-treated ATt-20 corticotroph cell-derived total RNA extracts demonstrated inhibition of POMC mRNA levels, and decreased PTTG mRNA expression, confirming decreased proliferative rates in the TZD-treated corticotroph pituitary tumor cells. 18S ribosomal RNA served to normalize RNA loading. Rat testis served as a positive control. M=RNA marker.

Following alternate splicing and post-translational processing of the pro-opio-melanocortin (POMC) gene, corticotroph cells express ACTH (White, A., et al., ACTH precursors: biological significance and clinical relevance, Clin. Endocrinol. 48:251–5 [1998]). Northern blot analysis of total RNA extracted from TZD-treated cells revealed that the ligand inhibited POMC mRNA abundance about 4-fold in AtT20 cells (FIG. 6A). In addition, an about 3-fold decrease in the proliferative marker, pituitary tumor transforming gene (PTTG) mRNA expression was observed, confirming decreased proliferative rates of the TZD-treated corticotroph pituitary tumor cells (FIG. 6A).

Figure 6B:
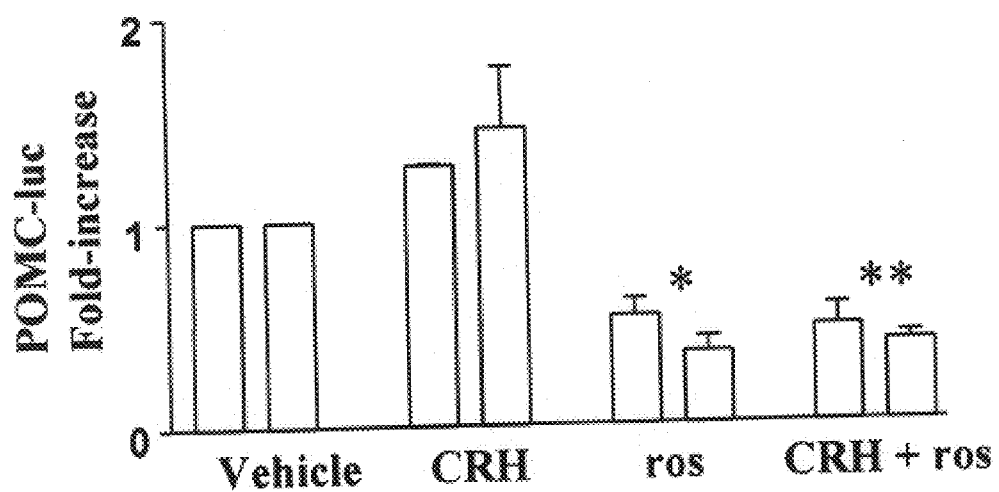
FIG. 6B demonstrates the effect of rosiglitazone (ros) on baseline and CRH-induced (50 nM) POMC transcription. AtT20 cells were pre-treated for 48 hours with rosiglitazone ($10^{-5}$ M). POMC-luc was transfected into AtT20 cells using lipofectamine. Results are expressed as fold induction of luciferase activity over control (vehicle), corrected for β-galactosidase activity (mean of 3 wells in 3 independent experiments±SEM). By ANOVA, and Bonferroni multiple comparison test. *, p<0.05 compared to control; **, p<0.05 compared to CRH.

CRH-treatment of AtT20 cells, transiently transfected with the POMC-promoter, resulted in a 1.6-fold increase in POMC-transcription. Rosiglitazone-treatment alone, or prior to CRH-treatment, abrogated basal and CRH-induced POMC transcription (FIG. 6B).

PPAR-γ Ligands Inhibit in Vivo Pituitary Tumor Growth

Figure 7A:
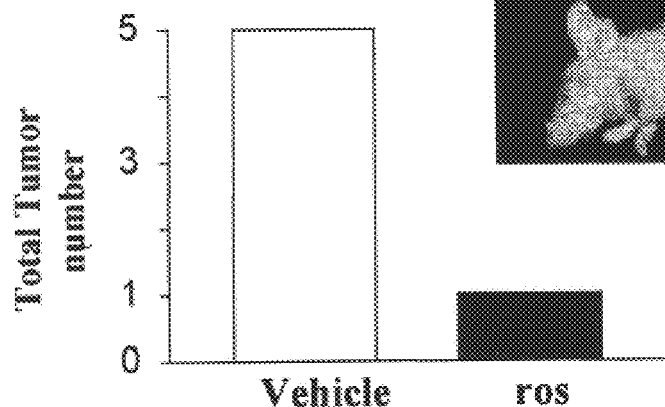
FIG. 7A graphically depicts tumor number in the vehicle-treated vs. rosiglitazone-treated mice.
Figure 7B:
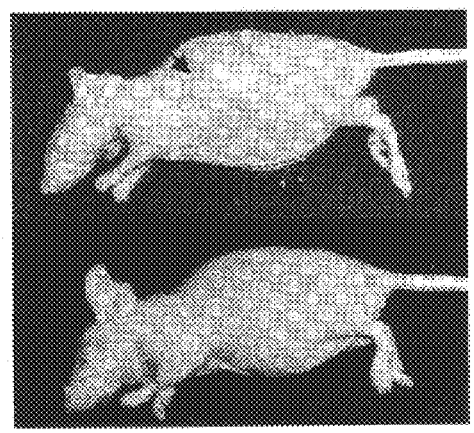
FIG. 7B is a representative picture of a rosiglitazone treated mouse and an untreated (control) mouse following subcutaneous innoculation of corticotroph pituitary tumor cells, wherein the untreated mouse developed a visible tumor (highlighted by the arrow) and the rosiglitazone-treated mouse did not.

As the TZDs exhibited anti-proliferative and pro-apoptotic effects in vitro, the effects of TZD-treatment were assessed on corticotroph pituitary tumor growth in vivo. Mouse corticotroph AtT20 pituitary tumor cells (about 200,000 cells) were inoculated subcutaneously in 4 week-old female athymic nude mice, and animals randomised to receive either oral rosiglitazone (150 mg/kg/ day) or vehicle. Baseline serum ACTH and corticosterone levels were comparable in the control and rosiglitazone-treated groups (data not shown, p=ns). After 4 weeks, four of five untreated control animals had developed large visible corticotroph tumors (1–2 cm diameter). In contrast, only one of five rosiglitazone-treated animals developed a small subcutaneous corticotroph cell tumor (0.1 cm diameter) (FIG. 7A and FIG. 7B). As depicted in FIG. 7B, the representative untreated mouse developed various phenotypic manifestations not present in the rosiglitazone-treated mouse. For instance, the untreated mouse developed a visible tumor (highlighted by the arrow), scaly skin with diminished elasticity, a shrunken and narrow head, and muscle atrophy.

Figure 7C:
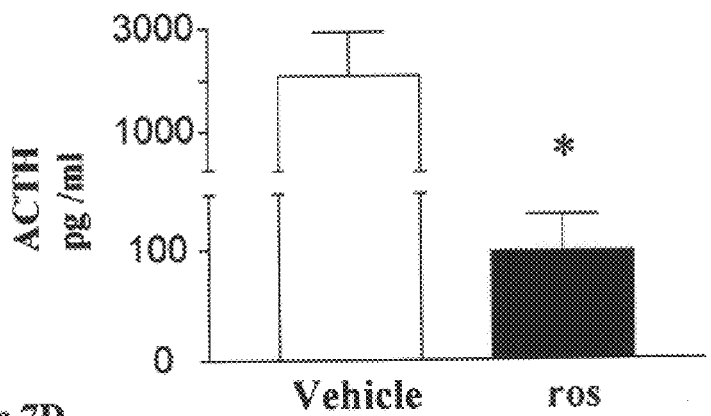
FIG. 7C illustrates the serum ACTH levels at baseline and after 4 weeks treatment with vehicle or rosiglitazone.
Figure 7D:
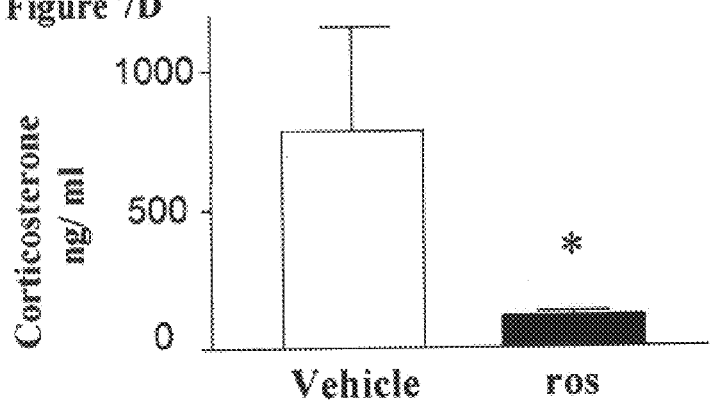
FIG. 7D illustrates the serum corticosterone levels at baseline after 4 weeks treatment with vehicle or rosiglitazone (ros). Number of animals per group=5. *, p<0.05.

Plasma ACTH and serum corticosterone levels were considerably lower in rosiglitazone-treated mice (ACTH; mean±SEM, 98±33 pg/ml; corticosterone; mean±SEM, 113±17 ng/mL) compared to vehicle-treated tumor-bearing animals (ACTH; mean±SEM; 2085±847 pg/ml; corticosterone; mean±SEM; 785±374) (p<0.05) (FIG. 7C and FIG. 7D).

Figure 8A:
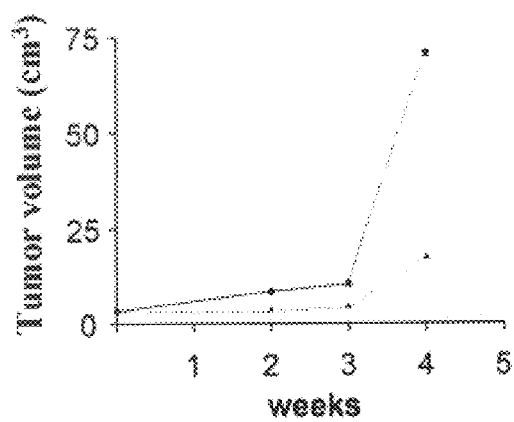
FIG. 8A is a representative growth curve illustrating that tumor growth was abrogated in the rosiglitazone-treated animals (p<0.05). The broken-line represents rosiglitazone-treated animals and the solid line represents vehicle treated animals.
Figure 8B:
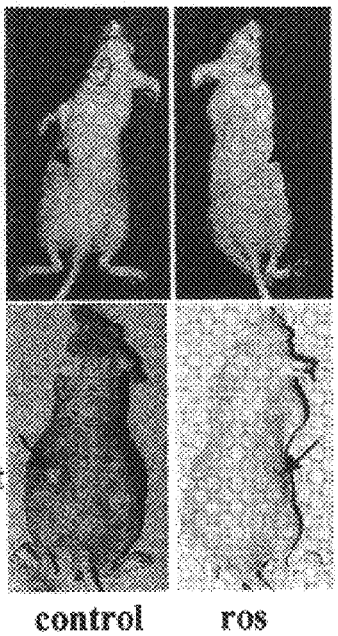
FIG. 8B depicts mice 3 weeks post-inoculation (upper panels) and after 3 weeks treatment (lower panels), and demonstrates the amelioration of the Cushing's phenotypic appearance for the mouse receiving the rosiglitazone treatment.
Figure 8C:
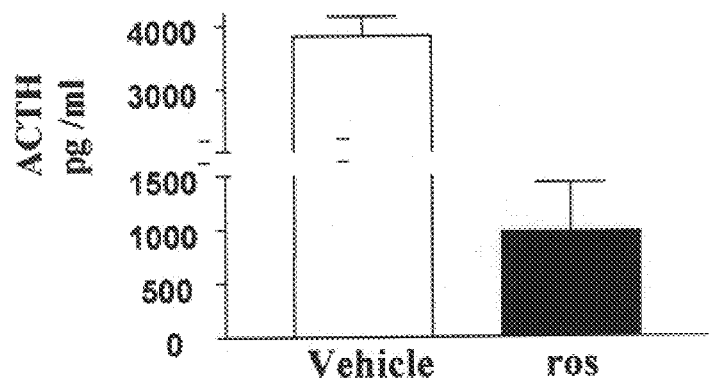
FIG. 8C demonstrates a reduction in serum ACTH in the rosiglitazone-treated vs. vehicle-treated animals.
Figure 8D:
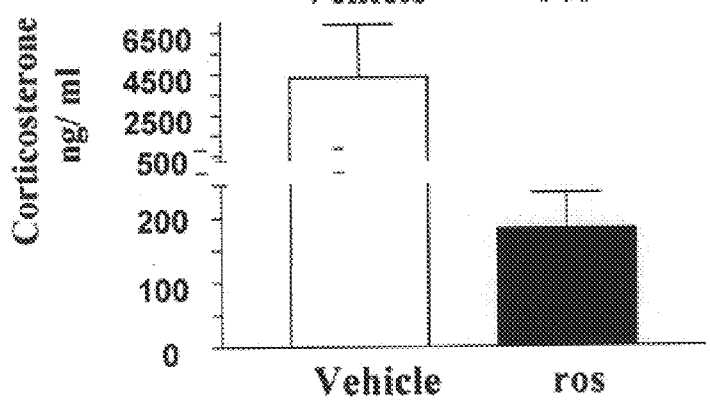
FIG. 8D depicts a reduction in corticosterone in the rosiglitazone-treated vs. vehicle-treated animals. * p<0.05.

Although TZD-treatment prevented experimental pituitary corticotroph tumor development in vivo, patients invariably present with established and actively growing pituitary tumors. The effects of TZD treatment were therefore tested on growth of already established pituitary corticotroph tumors, and steroid hormone levels in vivo. Mouse corticotroph pituitary tumor cells (AtT20) were innoculated subcutaneously in athymic nude mice, and tumors allowed to develop. By 3 weeks, all injected animals had developed large visible tumors, and were randomised to receive either oral rosiglitazone (150 mg/kg/ day) or vehicle. Baseline serum ACTH and corticosterone levels, and tumor volumes were not different in the groups subsequently randomized as control or treated groups (data not shown, p=ns). In both groups tumor growth continued, but was markedly abrogated (p<0.05) in 3 of 5 rosiglitazone-treated animals (a representative pair is depicted in FIG. 8B; see also FIG. 8A). All animals were euthanized at 6 weeks. The phenotypic appearance of the mice was strikingly different, and vehicle-treated mice were wasted, developed skin atrophy and appeared pigmented, with features of hypercorticolism (FIG. 8B). In contrast, rosiglitazone-treated mice continued to thrive and gain weight and did not display skin atrophy or pigmentation. In addition rosiglitazone treatment led to 75% reduction in plasma ACTH (FIG. 8C) (mean±SEM; controls, 3841±308 vs. ros-treated, 978±452 pg/mL, p=0.002), and a 96% reduction in serum corticosterone levels (FIG. 8D) (mean±SEM; controls, 4304±2593 vs. ros-treated, 181±56 ng/mL, p<0.05).

Figure 9A:
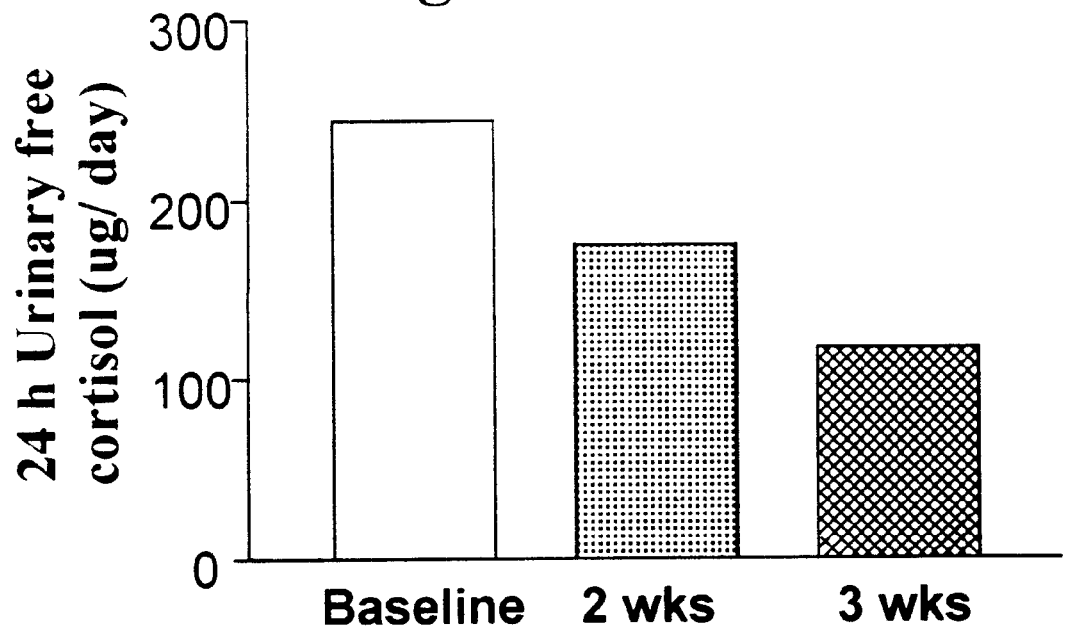
FIG. 9A demonstrates rosiglitazone suppression of urinary free cortisol (UFC) excretion in patient with Cushing's syndrome (24 hour UFC at baseline, and at 2-weeks and 3-weeks following rosiglitazone therapy, p<0.02).
Figure 9B:
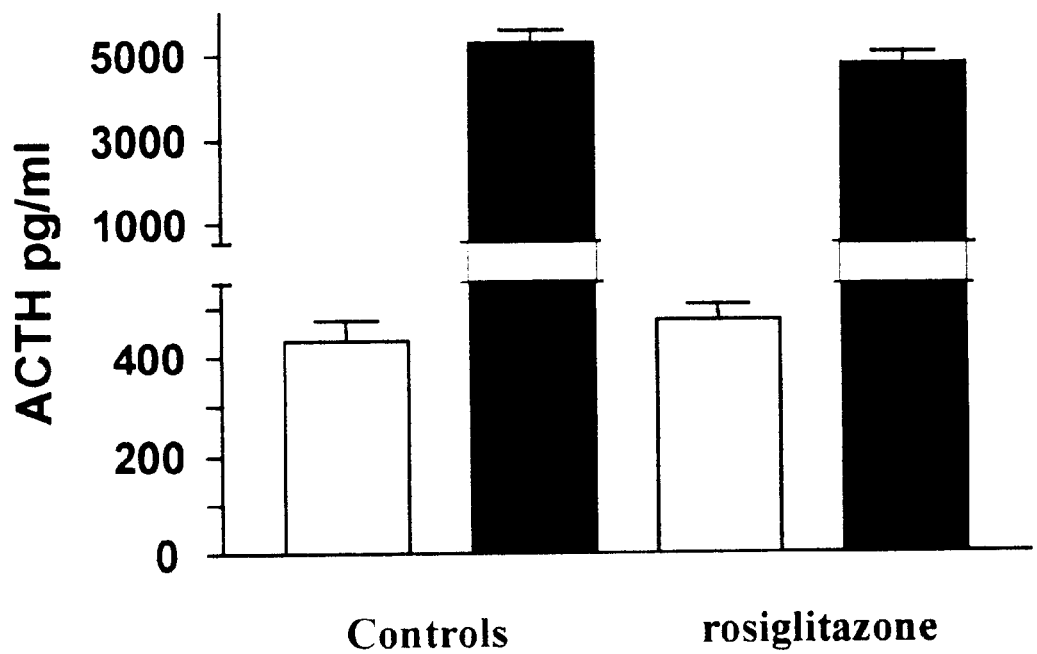
FIG. 9B illustrates that pituitary corticotroph responsiveness is preserved following long-term rosiglitazone-treatment in normal mice. Plasma ACTH (1400 h), unstressed and following 15 min restraint stress in normal female athymic Nu/Nu mice following 6 weeks oral treatment with vehicle or rosiglitazone (150 mg/kg/day). Unshaded bars indicate unstressed, shaded bars indicate stressed, p=not significant.

Preserved Pituitary-adrenal Function Following Chronic PPAR-γ Ligand Treatment in Normal Mice Given the observed pituitary corticotroph PPAR-γ expression, the TZD-induced decrease in plasma ACTH and corticosterone levels in vivo, and the potential use of these agents as medical therapy for Cushing's syndrome, effects of prolonged rosiglitazone administration were assessed on normal murine pituitary-adrenal function. Plasma ACTH (pg/mL) (FIG. 9B) and serum corticosterone ($\mu$g/mL) (not shown) were similar in rosiglitazone-treated (150 mg/kg for 6 weeks) and untreated normal athymic Nu/Nu mice, in both unstressed (quiet environment overnight) and stressed conditions (15 minutes restraint) (Mean±SEM ACTH, controls; baseline 434±40, stress-induced, 5278±312 vs. ros; baseline, 474±33, stress-induced 4764±292 pg/mL, p=ns) (FIG. 9B).

PPAR-γ Ligands Reduce Urinary Cortisol Excretion in Cushing's Syndrome

Rosiglitazone is approved for treating type II diabetes mellitus, which affects about 60% of patients with Cushing's syndrome (Ross, E. J., et al., Cushing's syndrome-killing disease: Discrimatory value of signs and symptoms aiding early diagnosis, Lancet 2:646–9 [1982]). A 29 year old female first presented 2 years ago with bruising, skin striae, 70 lb weight gain and hypertension. Evaluation confirmed the diagnosis of Cushing's syndrome due to an ACTH-secreting pituitary tumor, which was resected by transsphenoidal surgery. The patient presented again one year later with weight gain, labile hypertension, diabetes and confirmed recurrence of Cushing's syndrome. Prior to second pituitary surgery, rosiglitazone, 8 mg daily was administered for 3 weeks to control hyperglycemia. Baseline 24 hour urinary free cortisol excretion (UFC), was elevated at 244 pg/dL (normal 2–90 $\mu$g/dL), and decreased progressively, by 33% and 55% after 2 and 3 weeks rosiglitazone treatment respectively (FIG. 9A, p<0.02). It also was shown that pituitary corticotroph responsiveness is preserved following longterm rosiglitazone-treatment in normal mice (FIG. 9B). Plasma ACTH (1400 h), unstressed and following 15 min restraint stress in normal female athymic Nu/Nu mice following 6 weeks oral treatment with vehicle or rosiglitazone (150 mg/kg/day).

Moreover, based upon the findings set forth above, it is believed that treatment of subjects suffering from Cushing's syndrome tracing its etiology to tissues other than the pituitary also will benefit from the treatment method of the present invention. Specifically, it was shown above that administration of rosiglitizone inhibits ACTH promoter activity and ACTH MRNA expression. And, as ACTH is transcribed and secreted in the ectopic form of Cushings syndrome—from lung bronchial carcinoid tumors for example—it is believed that the treatment methods of the present invention also will inhibit ACTH secretion and the resultant hypercortisolism in subjects afflicted with ectopic Cushing's syndrome. Furthermore, it was demonstrated above that rosiglitazone treatment to mice harboring corticotroph tumors, in vivo, led to a dramatic decrease in corticosterone production, in addition to reduced ACTH secretion. These results indicate that PPAR-γ ligand treatment also will act to lower serum cortisol secretion in Cushing's syndrome due to adrenal tumors as well.

EXAMPLE 3

Materials and Methods

Patients and Tissues. Surgically resected pituitary adenoma samples were obtained from consecutive unselected patients after surgical resection, in accordance with institutional guidelines. For primary human pituitary cultures, pituitary tumor tissue, freshly obtained at surgery, was minced mechanically and digested for 45 minutes at 37° C. with 0.35% collagenase, and 0.1% hyaluronidase (Sigma Co., St. Louis, Mo.) in 10 mL DMEM medium. Cell suspensions were filtered and resuspended for 24 hours in low glucose DMEM containing 10% FBS, 2 mM glutamine and antibiotics (such as penicillin, streptomycin, and fungazone), prior to treatment with vehicle or rosiglitazone.

Cell Culture. Subconfluent rat GH3 and mouse αT3 pituitary (LH-secreting) cells were cultured in DMEM medium (Gibco BRL, Grand Island, N.Y.) supplemented with 15% fetal calf serum (FCS) and 2.5% horse serum or 10% FCS, respectively, and antibiotics (such as penicillin, streptomycin, and fungazone) at 37° C. in 5% $CO_2$ for 24 hours prior to treatment with troglitazone or rosiglitazone. Medium was replenished with ligands every 2 days, and cells maintained in serum-containing medium or in serum-free medium for up to 96 hours.

Cell Cycle Distribution. Following treatments, GH3, αT3, or human pituitary tumor cells were trypsinized, centrifuged (1500 rpm×2 min), washed with PBS, and treated with 20 g/mL Rnase A (Calbiochem, La Jolla, Cailf.). DNA was stained with 100 $\mu$g/mL propidium iodide (PI) for 30 min at 4° C. and protected from light, prior to analysis with a FACScan (Becton Dickinson, Franklin Lakes, N.J.). DNA histogram analysis was performed using the modFitLT software.

Apoptosis Assay: Annexin FITC by flow Cytometry. GH3, αT3 and human pituitary tumor cells were treated, washed in PBS, trypsinized, centrifuged, and washed prior to incubation with a FITC-labeled monoclonal Annexin antibody and PI for 30 min at room temperature according to manufacturer's instructions (Pharmingen, San Diego, Cailf.). About $1\times10^6$ cells were prepared and analyzed by flow cytometry, labeled nuclei (PI) were gated on light scatter to remove debris, and the percentage of Annexin-FITC positive cells determined. Annexin-FITC positive cells were also visualized with an Olympus BH2 immunofluorescent microscope.

Terminal Deoxynucleotidyltransferase-mediated dUTP Nick End Labeling (TUNEL). Apoptosis-induced nuclear DNA fragmentation was detected using the in situ cell death detection kit, TMR red (Roche Diagnostics, Indianapolis, Ind.) following the manufacturer's protocol. Briefly, 48 hours following TZD treatment, GH3, αT3 and human pituitary tumor cells were fixed in 4% weight per volume paraformaldehyde, permeabilized with 0.1% sodium citrate/0.6% Tween 20 (pH 7.4) for 2 min at 4° C. prior to incubation in Tunel reaction mix (TMR red/dNTP mix, TdT, and labeling buffer) for 60 min at 37° C. Slides were washed (3×5 min) in PBS/Triton/BSA (0.3%) and visualized on a an Olympus BH2 immunofluorescent microscope.

Northern blot analysis. Total RNA was extracted from cell cultures (about $3 \times 10^7$ cells/group) or from excised tissues with TRIzol (Gibco). Rat testis RNA served as a positive control for PTTG expression. Electrophoresed RNA was transferred to Hybond-n nylon membranes (Amersham International, Buckinghamshire, UK), and hybridized as previously described (Heaney, A. P., et al., Estrogen induced pituitary Tumor Transforming Gene (PTTG) and bFGF in Pituitary Tumor Pathogenesis, Nature Medicine 5:1317–1321 [1999]).

Immunocytochemical studies of pituitary glands. Surgically excised human pituitary tumor and normal pituitary autopsy tissues were obtained in accordance with institutional review board guidelines. Pituitary tissues from vehicle- or TZD-treated mice were obtained in accordance with institutional animal care and use committee guidelines. All tissues were fixed in 4% paraformaldehyde and processed for paraffin embeddment. Sections were immunostained using antibodies to human or mouse GH, PRL, FSH and/or LH (1:1000) (DAKO, Carpinteria, Cailf.), PPARγ (1:500) (Calbiochem, La Jolla, Cailf.) using both the avidin-biotin-peroxidase method, and counter-stained with haematoxylin. Negative controls were performed for each slide, using pre-absorbed or non-immune serum.

Western Blot Analysis. GH3, αT3, and pituitary tumor cells were seeded in 6-well plates for 24 hours (about 100,000 to 200,000 cells per well) prior to treatment with TZD's. Cells were then washed with PBS, and protein samples prepared in RIPA buffer and resolved under reducing conditions on 12% SDS-polyacrylamide gels using standard methods (Elstner, E., et al., Ligands for peroxisome proliferator-activated receptor-s and retinoic acid receptor inhibit growth and induce apoptosis of human breast cancer cells in vitro and in BNX mice. Proc. Natl. Acad. Sci. USA 95:8806–8811 [1998]). Resolved proteins were transferred to nitrocellulose membranes and probed with antibodies to Bcl-2 (1:500), Bax (1:1000), TRAIL (1:500), p53 (1:100) (all from Santa-Cruz, Cailf.), p-Rb (Ser 795) (1:1000), cleaved and uncleaved caspase-3 (1:500) (Cell Signaling, Beverly, Mass.) overnight at 4° C. After washing, membranes were incubated with appropriate IgG-horseradish peroxidase conjugates, and immunoreactive protein bands were visualized with ECL (Amersham, Buckinghamshire, UK). Total protein was normalized by reprobing with anti-actin antibody (1:5000, Sigma, St. Louis, Mo.) or Ponceau S staining, and protein bands quantified by densitometry (Video Densitometer model 620, Bio-Rad).

EXAMPLE 4

Results

PPAR-γ is Abundantly Expressed in Pituitary Tumors

Figure 10A:
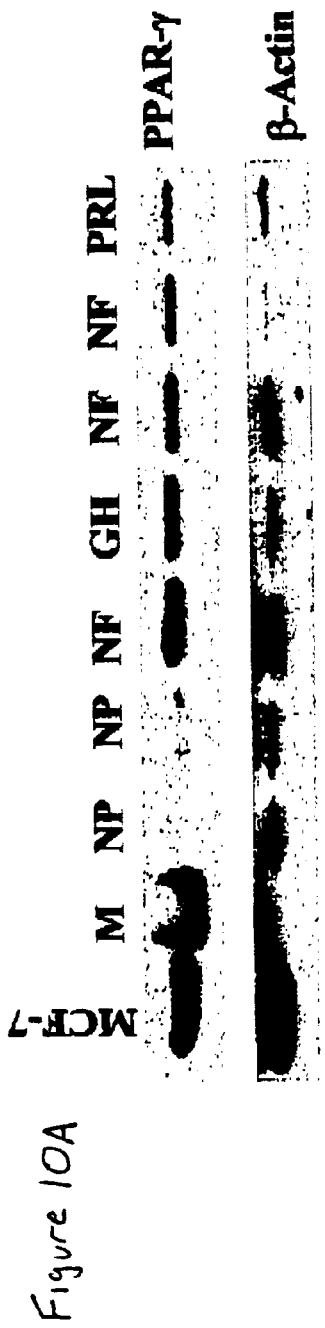
FIG. 10A, upper panel, demonstrates the results of a Western blot of 3 surgically resected non-functioning pituitary tumors (NF), of a surgically resected GH-secreting pituitary tumor (GH), and of a surgically resected PRL-secreting pituitary tumor (PRL) in comparison to PPAR-γ expression in two normal pituitary tissue-derived extracts (NP). β-actin immunoblotting confirmed equivalent total protein loading (FIG. 10A, lower panel). MCF-7 breast cancer cells served as a positive control, and M served as a protein marker (Amersham molecular weight protein marker).
Figure 10B:
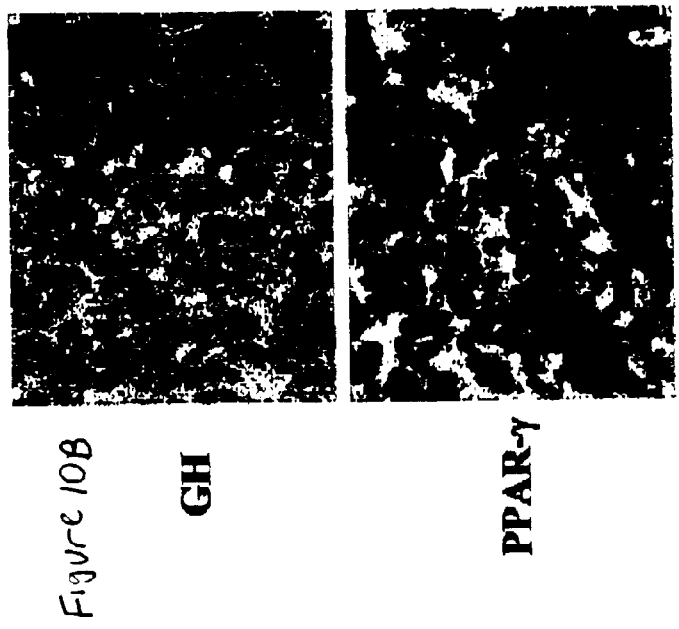
FIG. 10B depicts the results of the GH (upper panel) and PPAR-γ (lower panel) inumunocytochemical analysis of surgically resected GH-secreting pituitary tumor tissue (magnification×10), confirming PPAR-γ immunoreactivity.

PPAR-γ expression was assessed in 42 consecutive surgically resected pituitary tumor specimens, classified according to tumor immunopositivity (20 FSH- and/or LH-immunopositive, 5 PRL-, 3 GH-, and 5 PRL- and GH-immunopositive, and 9 non-functioning (absent hormone immunpositivity)). Western blotting of pituitary tumor-derived protein extracts revealed abundant PPAR-γ expression in all of 42 pituitary tumors examined, in comparison to modest PPAR-γ expression in nine normal pituitary-derived extracts (FIG. 10A). Immunocytochemical analysis demonstrated abundant PPAR-γ immunoreactivity localized to the pituitary adenoma cells of GH-secreting tumor tissue (FIG. 10B).

PPAR-γ Ligands Inhibits Pituitary Tumor Proliferation

Figure 11A:
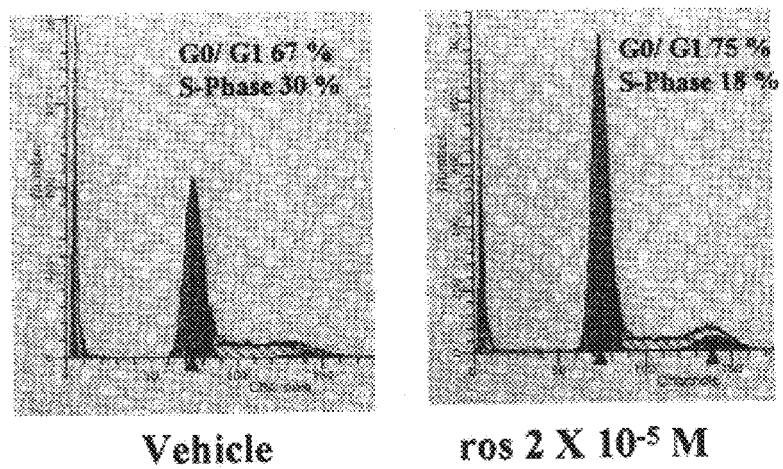
FIG. 11A shows FACS analysis of rosiglitazone $2\times10^{-5}$ M-treated rat GH3 cells and mouse alpha T3 gonadotroph cells.

To determine the functional significance of pituitary tumor PPAR-γ expression, the effects of PPAR-γ ligands was tested on pituitary tumor cells in vitro. Troglitazone or rosiglitazone-treatment (106 to 104 M) of GH3 (PRL- and GH-secreting), and αT3 (gonadotroph-secreting) and human pituitary tumor cells for up to 48 hours, in serum-free conditions, or up to 96 hours, for cells maintained in serum-repleted conditions, induced $G_0$-$G_1$ cell-cycle arrest (GH3: control, $G_1$ 75±4% vs. ros, $G_1$ 85±2%, p=0.009; αT3: control, $G_1$ 67±0.5% vs. ros, $G_1$ 75±0.5%, p=0.01), and led to decreased number of cells in S-phase (GH3: control, 18±0.05% vs. ros, 12±0.5%, p=0.001; αT3: control, 31±0.5% vs. ros, 16±2.5%, p=0.03) (FIG. 11A).

Figure 11B:
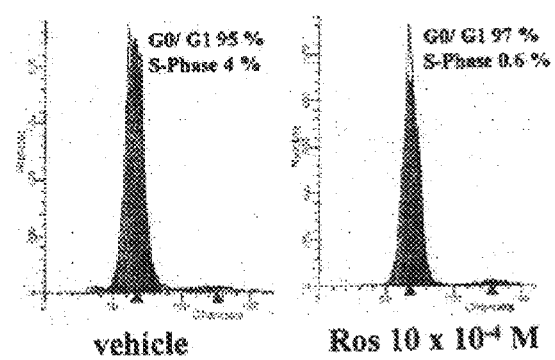
FIG. 11B shows FACS analysis of rosiglitazone $10\times10^{-5}$ M-treated human pituitary tumor cells in vitro.
Figure 11C:
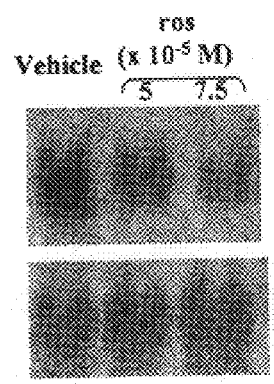
FIG. 11C reveals decreased expression of the proliferative marker PTTG in alpha T3 gonadotroph cells treated with rosiglitazone vs. the controls.
Figure 11D:
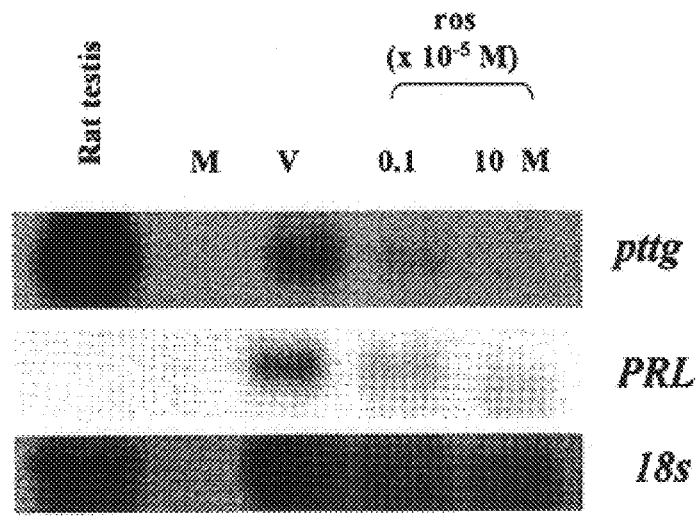
FIG. 11D reveals decreased pituitary tumor-transforming gene (PTTG) (upper panel) and PRL (middle panel) mRNA expression in rat GH3 cells.
Figure 11E:
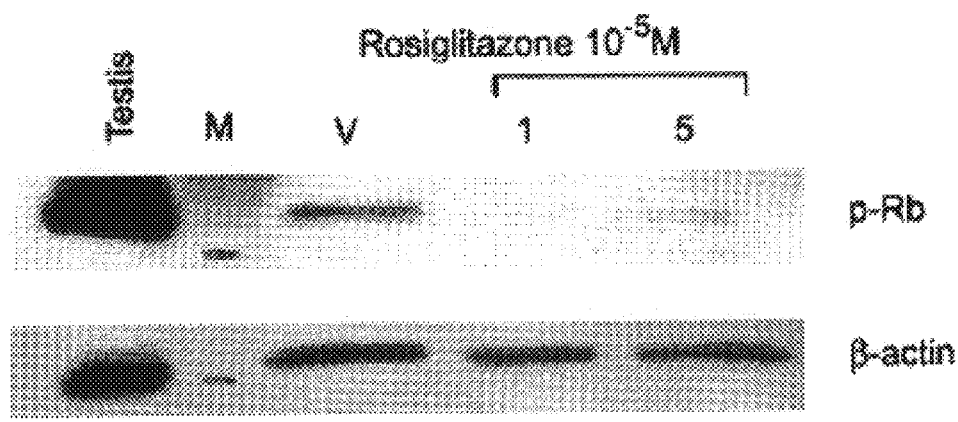
FIG. 11E reveals decreased expression of $Ser^{794}$ phosphorylated retinoblastoma protein in human non-functioning pituitary tumors. Rat testis served as a positive control. 18s (FIG. 11D, lower panel) and β-actin (FIG. 11E, lower panel) confirmed equivalent total RNA and protein loading, respectively; "M" represents protein marker (Amershamn molecular weight protein marker).

Northern blot analysis of total RNA extracted from TZD-treated rat GH3 and mouse αT3 cells revealed that the ligand induced an about 3-fold decrease in the proliferative marker, pituitary tumor transforming gene (PTTG) mRNA expression confirming decreased proliferative rates of TZD-treated gonadotroph tumor cells (FIGS. 11B and 11C). Western blot analysis of protein extracts derived from TZD-treated human non-functioning pituitary tumor cells showed an about 60% decrease in $Ser^{795}$ phosphorylated retinoblastoma protein expression (FIG. 11D), indicating a possible mechanism for the observed $G_0/G_1$ cell-cycle arrest.

PPAR-γ Ligands Induce Pituitary Tumor Apoptosis in Vitro

Figure 12A:
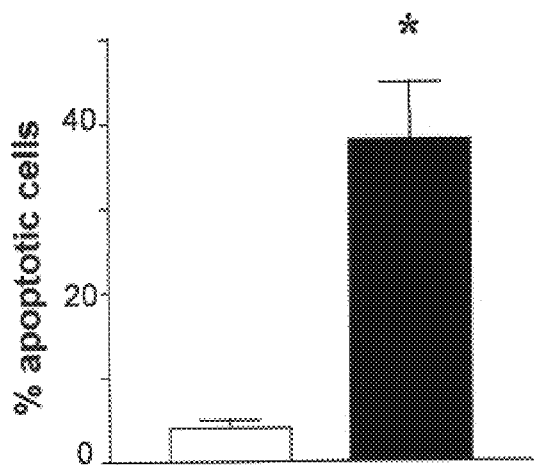
Figure 12B:
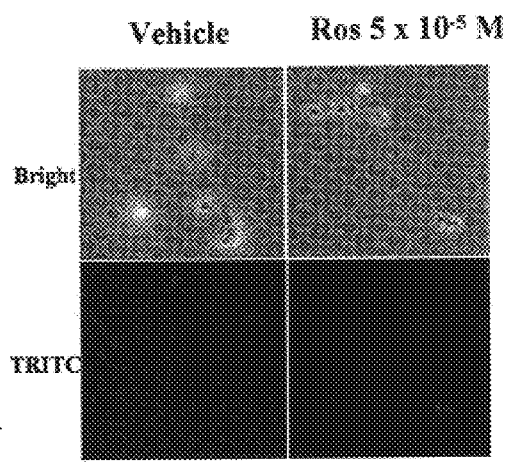
Figure 12B:
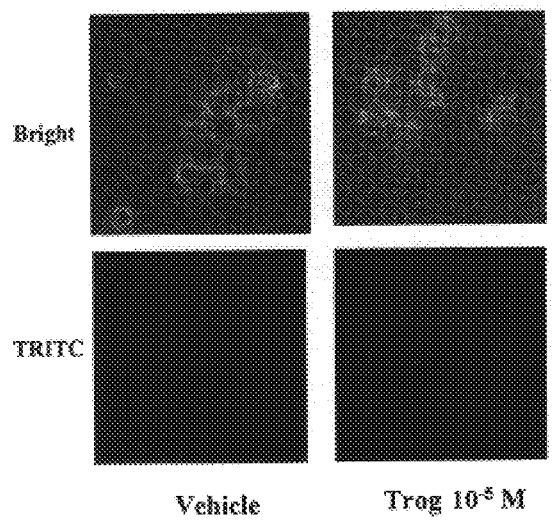
Figure 12:
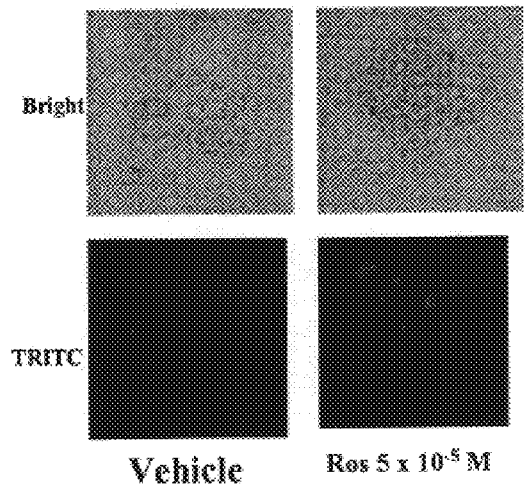
FIG. 12 illustrates that treatment with TZDs induced cell death and apoptosis in various cell types.

Rosiglitazone ($10^{-5}$ to $10^{-4}$ M) treatment of rat GH3, murine αT3, and human pituitary tumor cells for 96 hours demonstrated an increase in Annexin-FITC immunoreactive cells, and enhanced apoptosis (p<0.001). FACS and TUNEL analysis confirmed that TZD induced cell death, and increased apoptosis about 3-fold (FIG. 12A, FIG. 12B, and FIG. 12C) (% apoptosis: control, 33±3 vs. ros, $10^{-6}$ M 47±4; ros, $10^{-5}$ M 69±7%, p<0.0002).

Western blot analysis of protein extracts derived from TZD-treated nonfunctioning pituitary tumor cells showed decreased expression of the anti-apoptotic protein Bcl-2, and increased levels of pro-apoptotic Bax and p53 expression, suggesting a potential mechanism for the observed increased apoptosis. An about 4-fold increase in cleaved caspase-3 and a concomitant decrease in total caspase-3 resulted from TZD-treatment, and were consistent with enhanced apoptosis.

PPAR-γ Ligands Inhibit Pituitary Tumor Growth, GH, PRL and LH Secretion in Vivo

Figure 13A:
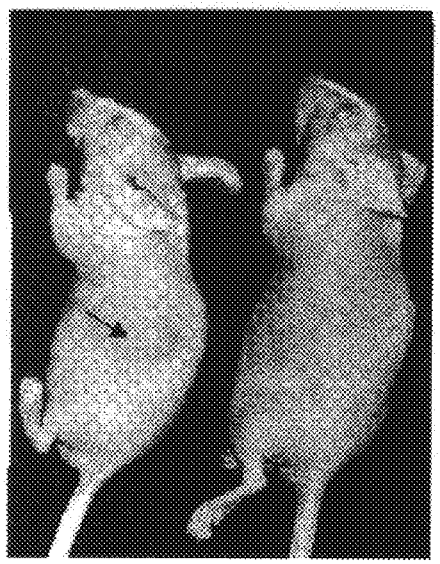
FIG. 13A is a representative picture of a rosiglitazone treated mouse (right) and an untreated control (left) mouse 4 weeks following subcutaneous innoculation of GH3 pituitary tumor cells, wherein the untreated mouse developed a visible tumor (highlighted by the arrow) while the rosiglitazone-treated mouse did not.
Figure 13B:
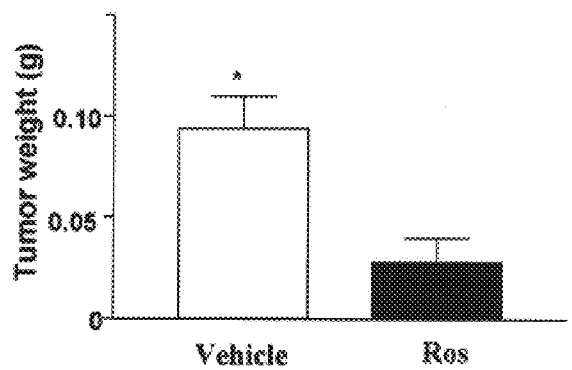
FIG. 13B graphically depicts total tumor weight in the vehicle-treated vs. rosiglitazone-treated mice after 4 weeks treatment with vehicle or rosiglitazone as indicated above.

As the TZD's exhibited anti-proliferative and pro-apoptotic effects in vitro, the effects of TZD-treatment were assessed on somato-lactotroph pituitary tumor growth in vivo. Somatolactotroph (GH3) (about 200,000 cells) were inoculated subcutaneously in 4 week-old female athymic nude mice, and animals randomized to receive either oral rosiglitazone (150 mg/kg/day) or vehicle. After 4 weeks, 3 of 4 vehicle-treated mice developed large visible tumors, necessitating their euthanitization. In contrast, 3 of 5 rosiglitazone-treated mice developed visible subcutaneous tumors (1–2 cm diameter), but tumor weight was markedly less in rosiglitazone-treated mice (Control, 0.13±0.01 vs. ros, 0.04±0.01 g, p=0.008) (FIG. 13A and FIG. 13B). As depicted in FIG. 13A, the representative untreated mouse developed various phenotypic manifestations not present in the rosiglitazone-treated mouse. For instance, the untreated mouse developed a visible tumor (highlighted by the arrow).

Figure 13C:
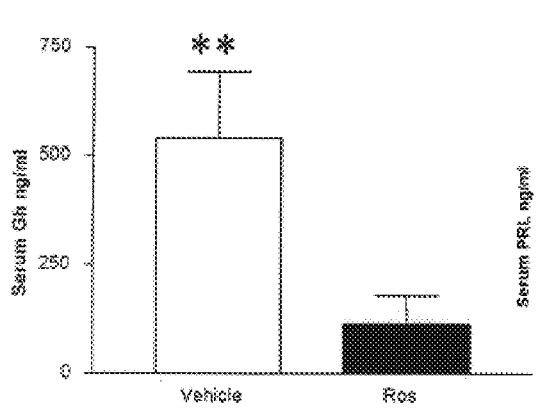
FIG. 13C illustrates the serum GH levels in vehicle- or rosiglitazone-treated mice after 4 weeks administration.
Figure 13D:
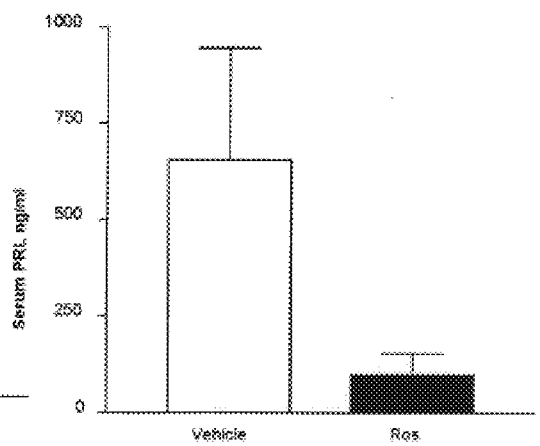
FIG. 13D illustrates the serum PRL levels in the tumor bearing mice after 4 weeks treatment with vehicle or rosiglitazone. n (number of animals per group)=5. *, p=0.008, p=0.03.

In addition, serum PRL (Control, 656±289 vs. ros, 95±58 ng/mL, p=ns) and GH (Control, 545±153 vs. ros, 114±66 ng/mL, p=0.03) levels were lower in rosiglitazone-treated mice relative to the vehicle-treated mice (FIG. 13C and FIG. 13D).

Figure 14A:
FIG. 14A is a representative picture of a rosiglitazone-treated mouse ("Ros") and an untreated (control) mouse 4 weeks following commencement of administration of treatment. The untreated (control) mouse in the picture developed numerous large visible tumors. In contrast, the rosiglitazone-treated mouse (Ros), while it did develop visible tumors, developed significantly smaller ones.
Figure 14B:
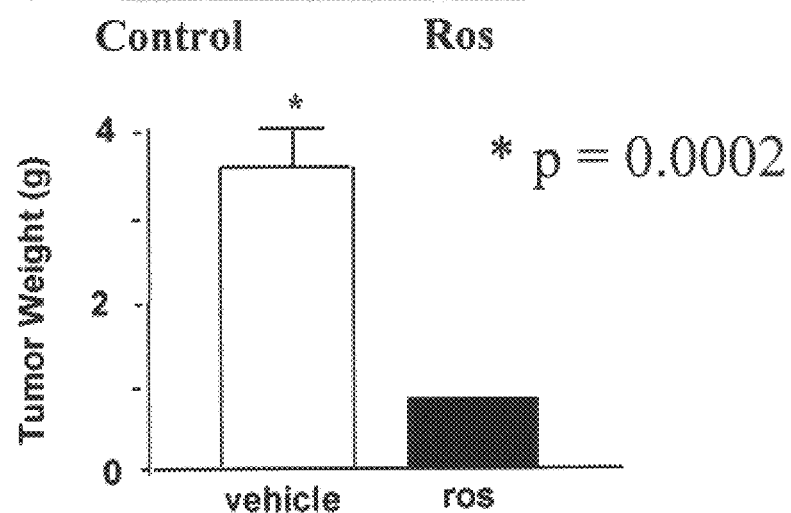
FIG. 14B graphically depicts total tumor weight in the vehicle-treated vs. rosiglitazone-treated mice after 6 weeks treatment with vehicle or rosiglitazone as indicated above.
Figure 14C:
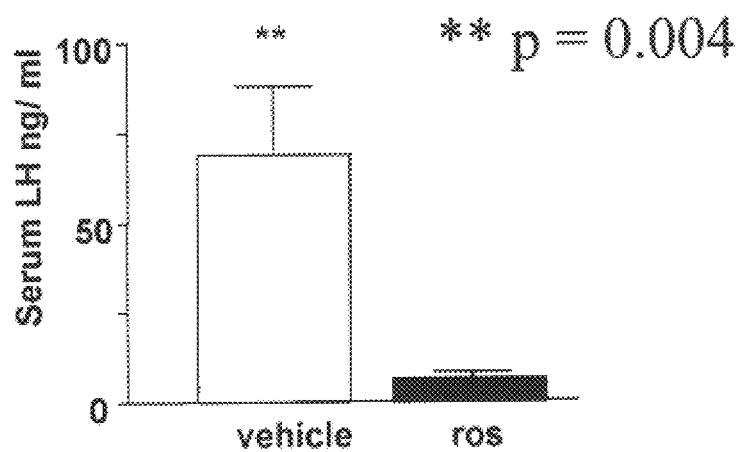
FIG. 14C illustrates the serum LH levels after 6 weeks treatment with vehicle or rosiglitazone. n=5. *, p=0.0002, **, p=0.004.

In separate parallel similarly conducted studies, gonadotroph tumor cells (LβT2) were innoculated in mice as above. Tumor weights and plasma LH (control, 69±19 ng/mL vs. ros, 6.8±1.0 ng/mL, p=0.004) levels were considerably lower in 6-week rosiglitazone-treated mice compared to vehicle-treated tumor-bearing animals; (Gonadotroph: control, 3.44±0.42 vs. ros, 0.81±0.19 g, P<0.002) (FIG. 14B and FIG. 14C), confirming the potent antitumor PPAR-ligand effects in vivo, and demonstrating the role of PPAR-γ ligands as therapy in gonadotroph and non-functioning pituitary tumors.

Figure 15A:
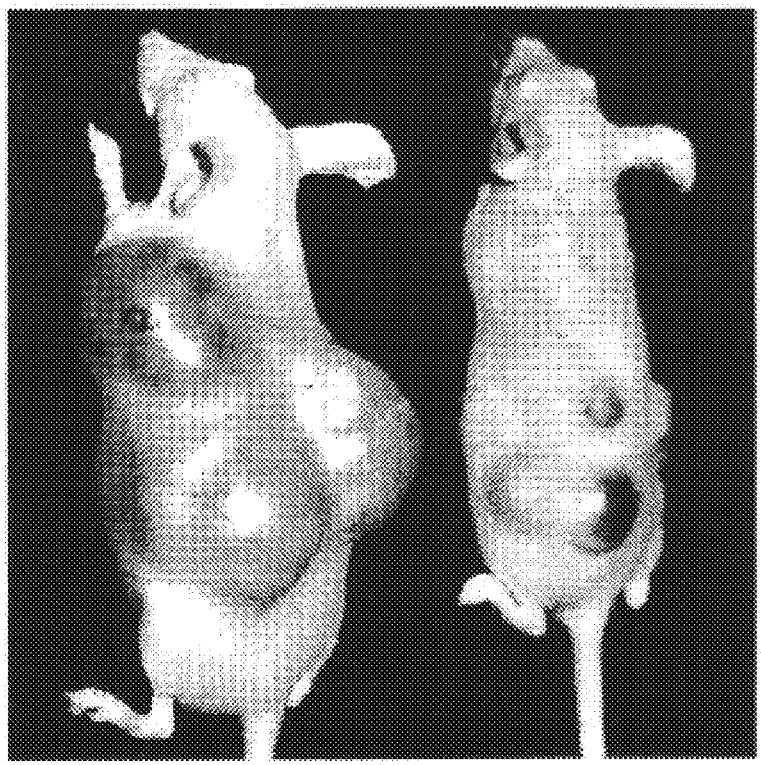
FIG. 15A is a representative picture of a rosiglitazone-treated mouse (right) and an untreated control mouse (left) as per above. The untreated (control) mouse in the picture developed numerous large visible tumors. In contrast, the rosiglitazone-treated mouse (ros), while it did develop visible tumors, developed significantly smaller ones.
Figure 15B:
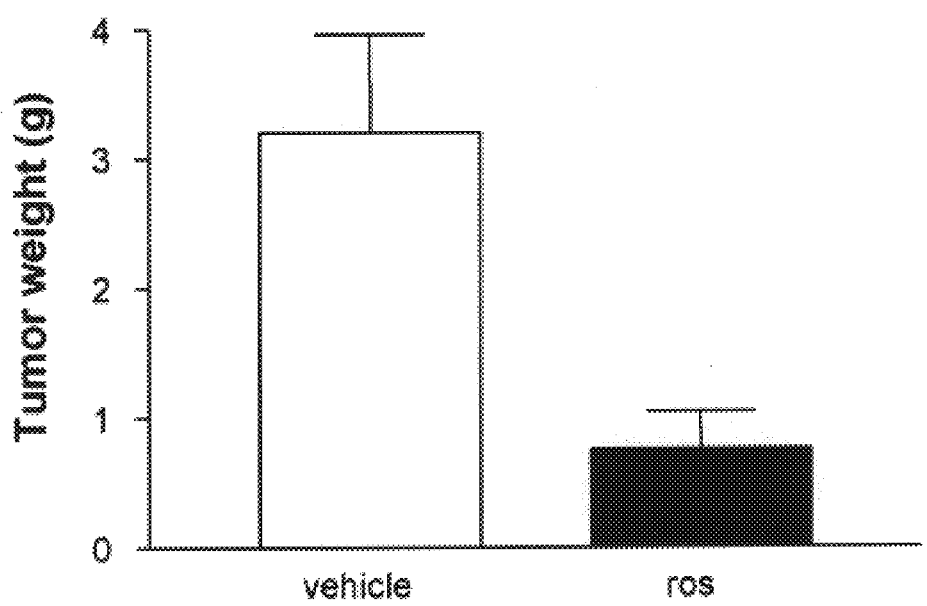
FIG. 15B graphically depicts total tumor weight in the vehicle-treated vs. rosiglitazone-treated mice after 6 weeks treatment with vehicle or rosiglitazone ("ros") as indicated above. Tumor weights significantly were abrogated in the rosiglitazone-treated animals. *, p=0.005.

As patients invariably present with already established and actively growing pituitary tumors, the effects of TZD treatment were therefore tested on growth of already established pituitary gonadotroph tumors in vivo. Mouse gonadotroph pituitary tumor cells (αT3) were inoculated subcutaneously in athymic nude mice, and tumors allowed to develop. By 3 weeks, all injected animals had developed large visible tumors, and were then randomized to receive either oral rosiglitazone (150 mg/kg/day) or vehicle for 6 weeks treatment. Baseline tumor volumes were not different in the groups subsequently randomized as control or treated groups (data not shown, p=ns). In both groups tumor growth continued, but final tumor weights were markedly abrogated in all of four 6 week treated rosiglitazone-treated animals (Vehicle, 3.2±0.76 vs. ros, 0.76±0.29 g, p=0.005). (FIG. 15A and FIG. 15B).

While the invention has been described in detail with reference to certain preferred embodiments thereof, it should be understood by those skilled in the art that modifications and variations to the embodiments and exemplary disclosure provided are within the spirit and scope of the invention as described and claimed in this patent.

We claim:

1. A method for treating a non-cancerous pituitary tumor in a mammal, comprising:

administering to a mammal having a non-cancerous pituitary tumor an effective amount of at least one peroxisome proliferator activated receptor gamma ligand.

2. The method of claim 1, wherein the at least one peroxisome proliferator activated receptor gamma ligand is a thiazolidinedione compound.

3. The method of claim 1, wherein the thiazolidinedione compound is selected from the group consisting of rosiglitazone, pioglitazone, and troglitazone.

4. The method of claim 1, wherein the pituitary tumor is an ACTH-secreting, LH-secreting, GH-secreting, or PRL-secreting pituitary tumor.

5. The method of claim 1, wherein the pituitary tumor is a non-functioning pituitary tumor.

6. A method for preventing the formation of a non-cancerous pituitary tumor in a mammal, comprising:

administering to a mammal at higher than normal risk for developing a non-cancerous pituitary tumor an effective amount of at least one peroxisome proliferator activated receptor gamma ligand.

7. A method for preventing the recurrence of a non-cancerous pituitary tumor in a mammal, comprising:

administering to a mammal, said mammal previously having had a detectable, non-cancerous pituitary tumor that was eliminated, an effective amount of at least one peroxisome proliferator activated receptor gamma ligand, whereby recurrence of the non-cancerous pituitary tumor is prevented.

8. A method for treating a mammal exhibiting one or more symptoms of Cushing's syndrome resulting from hypersecretion of adrenocorticotrophic hormone (ACTH), comprising:

administering to the mammal an effective amount of at least one peroxisome proliferator activated receptor gamma ligand.

9. The method of claim 8, wherein the symptom of Cushing's syndrome is steroid hypersecretion.

10. The method of claim 8, wherein the symptom of Cushing's syndrome is elevated urinary cortisol excretion.

11. A method for treating a non-functioning, non-cancerous pituitary tumor in a mammal, comprising:

administering to a mammal having a non-functioning, non-cancerous pituitary tumor an effective amount of at least one peroxisome proliferator activated receptor gamma ligand.

12. The method of claim 11, wherein the at least one peroxisome proliferator activated receptor gamma ligand is a thiazolidinedione compound.

13. The method of claim 11, wherein the thiazolidinedione compound is selected from the group consisting of rosiglitazone, pioglitazone, and troglitazone.

14. A method for treating a non-functioning, non-cancerous pituitary tumor in a mammal, comprising administering to a mammal having a non-functioning, non-cancerous pituitary tumor an effective amount of a thiazolidinedione compound.

15. A method for treating a non-functioning, non-cancerous pituitary tumor in a mammal, comprising:

administering to a mammal having a non-functioning, non-cancerous pituitary tumor an effective amount of a thiazolidinedione compound selected from the group consisting of rosiglitazone, pioglitazone, and troglitazone.

* * * * *